(12) United States Patent
Rezach et al.

(10) Patent No.: US 11,672,575 B2
(45) Date of Patent: Jun. 13, 2023

(54) SURGICAL INSTRUMENT AND METHOD

(71) Applicant: Warsaw Orthopedic, Inc., Warsaw, IN (US)

(72) Inventors: William A. Rezach, Covington, TN (US); Lawrence G. Lenke, New York, NY (US); Charles Fisher, Vancouver (CA); Marcel Dvorak, Vancouver (CA); Daniel M. Sciubba, Reisterstown, MD (US); Christopher Shaffrey, Charlottesville, VA (US); Sigurd H. Berven, San Francisco, CA (US); Ronald Lehman, Tenafly, NJ (US); Jason M. May, St. Johns, FL (US); Nicholas D. Fletcher, Atlanta, GA (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 519 days.

(21) Appl. No.: 16/560,587

(22) Filed: Sep. 4, 2019

(65) Prior Publication Data

US 2021/0059724 A1 Mar. 4, 2021
US 2022/0000524 A9 Jan. 6, 2022

Related U.S. Application Data

(63) Continuation-in-part of application No. 16/395,574, filed on Apr. 26, 2019, now Pat. No. 11,278,325, and a continuation-in-part of application No. 14/645,232, filed on Mar. 11, 2015, now Pat. No. 10,285,740.

(51) Int. Cl.
*A61B 17/70* (2006.01)
*A61B 17/88* (2006.01)

(52) U.S. Cl.
CPC ...... *A61B 17/7082* (2013.01); *A61B 17/7002* (2013.01); *A61B 17/7059* (2013.01); *A61B 17/7083* (2013.01); *A61B 17/8886* (2013.01)

(58) Field of Classification Search
CPC ........... A61B 17/7002; A61B 17/7059; A61B 17/7082; A61B 17/7083; A61B 17/8886
See application file for complete search history.

(56) References Cited

U.S. PATENT DOCUMENTS

| | | | |
|---|---|---|---|
| 2,370,407 A | 2/1945 | McCartney | |
| 4,438,769 A | 3/1984 | Pratt et al. | |
| 4,570,624 A | 2/1986 | Wu | |
| 4,763,548 A | 8/1988 | Leibinger et al. | |
| 4,887,020 A | 12/1989 | Graham | |
| 5,649,931 A * | 7/1997 | Bryant | A61B 17/8891 606/104 |
| 5,667,513 A | 9/1997 | Torrie et al. | |
| 6,189,422 B1 | 2/2001 | Stihl | |
| 6,860,889 B2 | 3/2005 | Bonati et al. | |
| 7,090,680 B2 | 8/2006 | Bonati et al. | |
| 7,575,581 B2 | 8/2009 | Lovell | |
| 7,854,751 B2 | 12/2010 | Sicvol et al. | |
| 7,988,699 B2 | 8/2011 | Martz et al. | |

(Continued)

*Primary Examiner* — Nicholas J Plionis
(74) *Attorney, Agent, or Firm* — Fox Rothschild LLP

(57) ABSTRACT

A surgical instrument having a first member engageable with a first end of a fastener having a second end configured to penetrate tissue. A second member includes an expandable member configured for engaging the first end. Systems and methods are disclosed.

19 Claims, 18 Drawing Sheets

(56) References Cited

U.S. PATENT DOCUMENTS

| | | |
|---|---|---|
| 8,303,602 B2 | 11/2012 | Biedermann et al. |
| 8,608,746 B2 | 12/2013 | Kolb et al. |
| 8,876,869 B1 | 11/2014 | Schafer et al. |
| 9,084,642 B2 | 7/2015 | Peultier |
| 9,149,308 B2 | 10/2015 | Biedermann et al. |
| 9,198,698 B1 * | 12/2015 | Doose ................ A61B 17/7085 |
| 9,326,798 B2 | 5/2016 | Kolb et al. |
| 9,510,874 B2 | 12/2016 | Kruger |
| 9,517,092 B2 | 12/2016 | Biedermann et al. |
| 9,532,814 B2 | 1/2017 | Harper |
| 9,572,605 B2 | 2/2017 | Shipp |
| 9,615,862 B1 | 4/2017 | Doubler et al. |
| 9,888,948 B2 | 2/2018 | Petit |
| 9,968,385 B2 | 5/2018 | Biedermann |
| 10,058,359 B2 | 8/2018 | Black et al. |
| 10,123,826 B2 | 11/2018 | Harper |
| 2002/0020255 A1 | 2/2002 | Simon et al. |
| 2006/0111713 A1 | 5/2006 | Jackson |
| 2007/0078460 A1 * | 4/2007 | Frigg ................ A61B 17/7002 606/86 A |
| 2012/0022597 A1 * | 1/2012 | Gephart ............ A61B 17/7091 606/279 |
| 2015/0066089 A1 * | 3/2015 | Nelson ............... A61B 17/7091 606/86 A |
| 2021/0068881 A1 | 3/2021 | Wall |

* cited by examiner

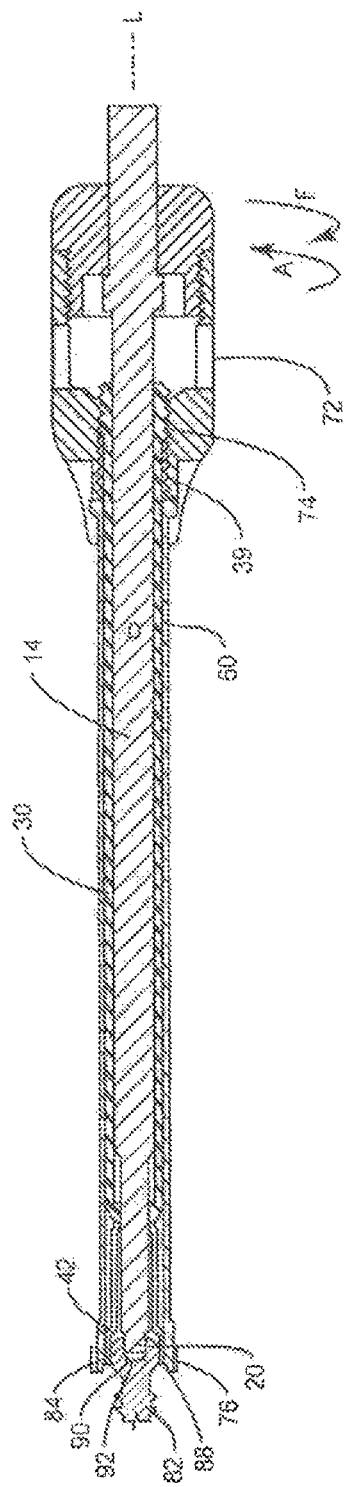

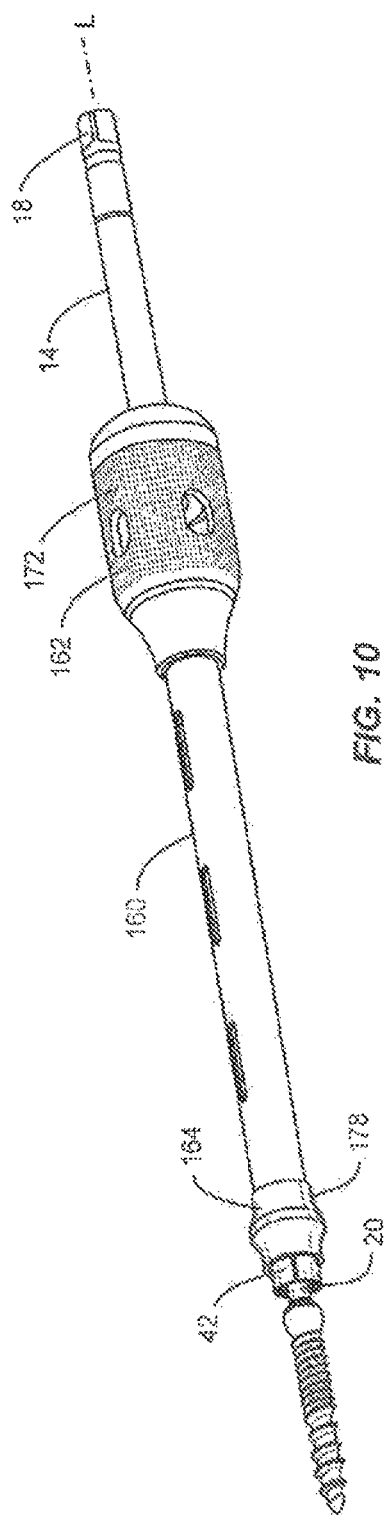
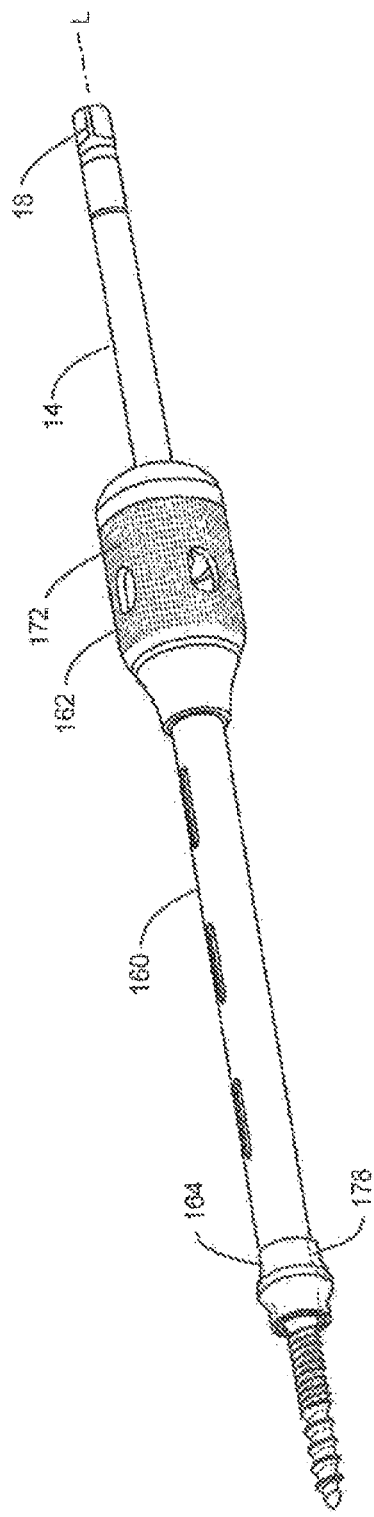

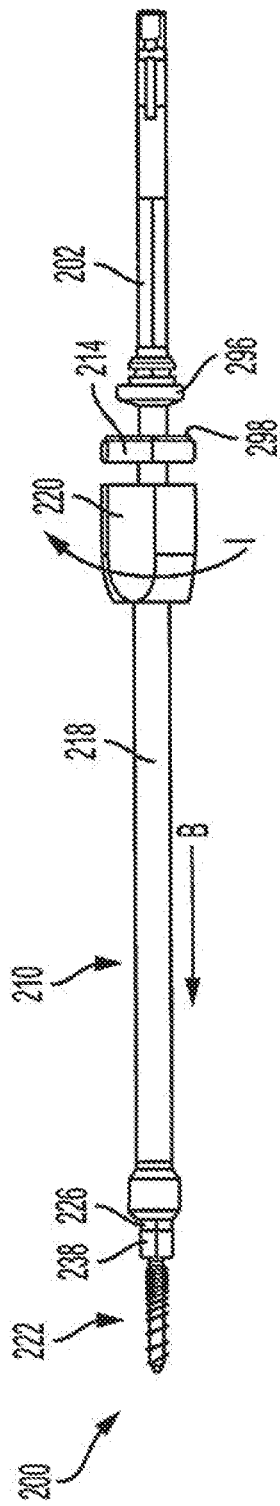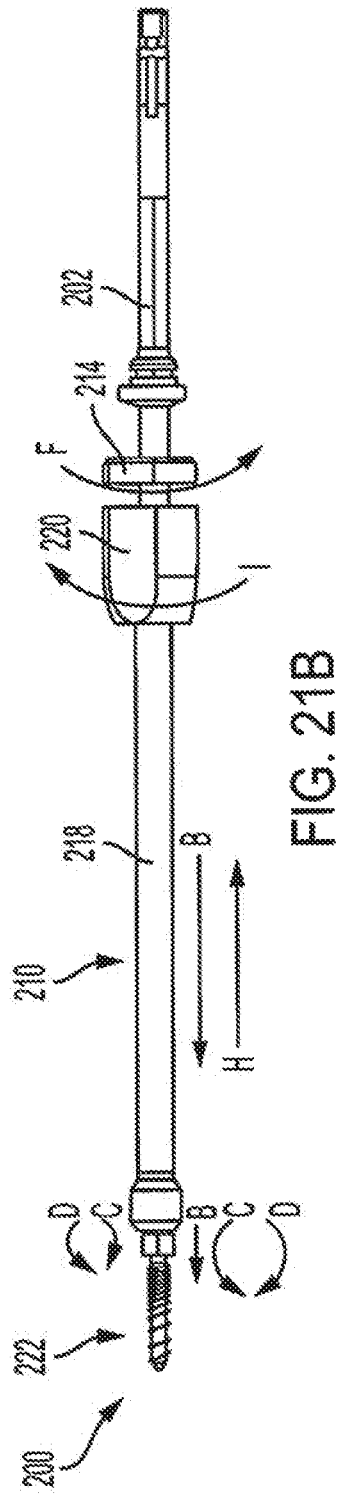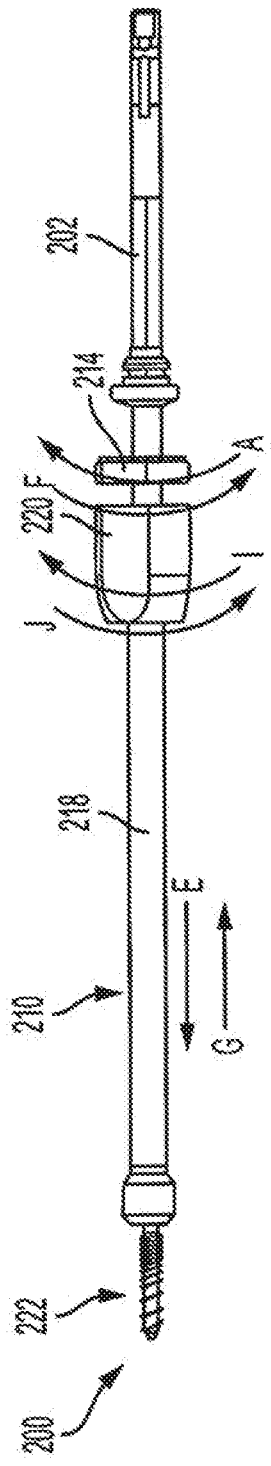

SURGICAL INSTRUMENT AND METHOD

CROSS-REFERENCE TO RELATED APPLICATIONS

This application is a continuation-in-part of U.S. Nonprovisional application Ser. No. 16/395,574, which was filed on Apr. 26, 2019 and is a continuation-in-part of U.S. Nonprovisional patent application Ser. No. 14/645,232, entitled "SURGICAL INSTRUMENT AND METHOD", filed Mar. 11, 2015, now U.S. Pat. No. 10,285,740. The entire contents of each which is incorporated herein by reference in its entirety.

TECHNICAL FIELD

The present disclosure generally relates to medical devices for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to the exterior of two or more vertebral members. This disclosure describes an improvement over these prior art technologies.

SUMMARY

In one embodiment, a surgical instrument is provided. A surgical instrument includes a first member engageable with a first end of a fastener having a second end configured to penetrate tissue. A second member includes an expandable member configured for engaging the first end. In some embodiments, systems and methods are disclosed.

BRIEF DESCRIPTION OF THE DRAWINGS

The present disclosure will become more readily apparent from the specific description accompanied by the following drawings, in which:

FIG. 5 is a cross-section view of the components shown in FIG. 1;

FIG. 10 is a perspective view of components of a surgical system in accordance with the principles of the present disclosure;

FIG. 11 is a perspective view of the components shown in FIG. 10;

FIGS. 21A-21C are perspective views of the components of the surgical system as shown in FIG. 16.

DETAILED DESCRIPTION

Figure 1:
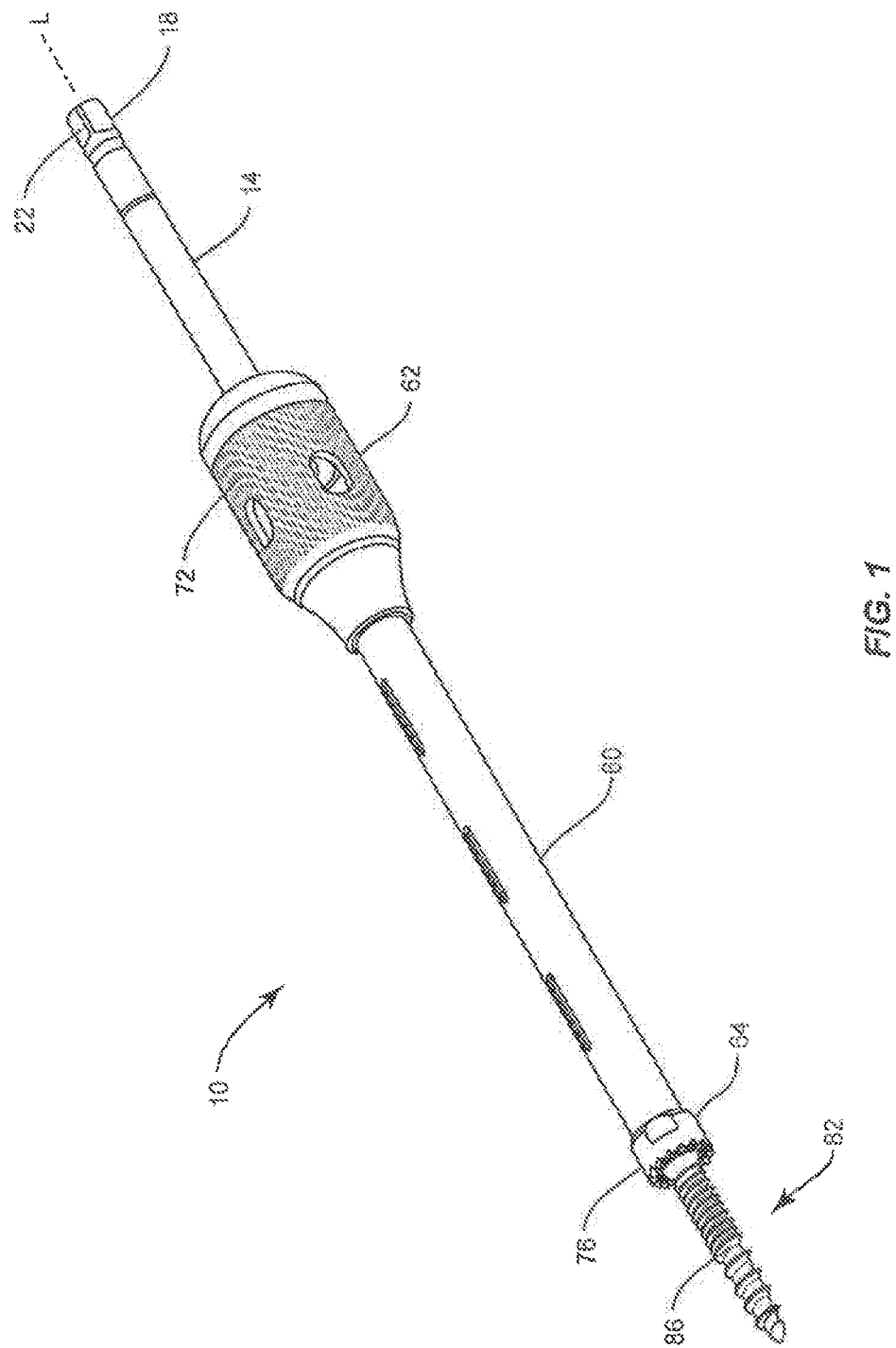
FIG. 1 is a perspective view of components of a surgical system in accordance with the principles of the present disclosure.
Figure 2:
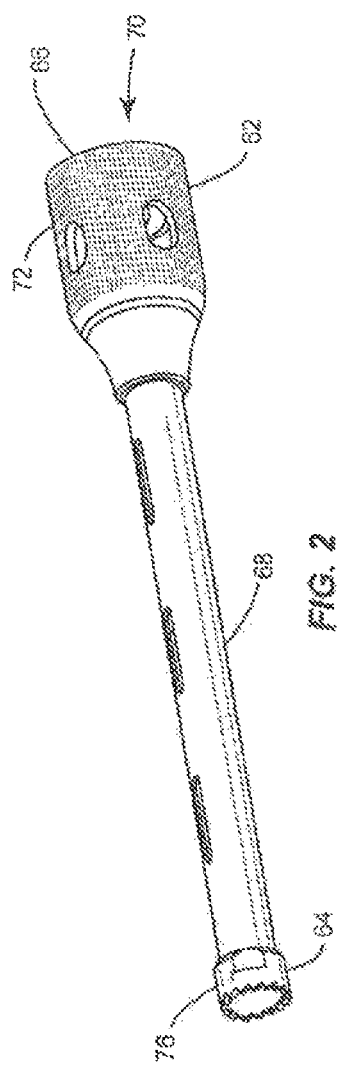
FIG. 2 is a perspective view of the components shown in FIG. 1.
Figure 3:
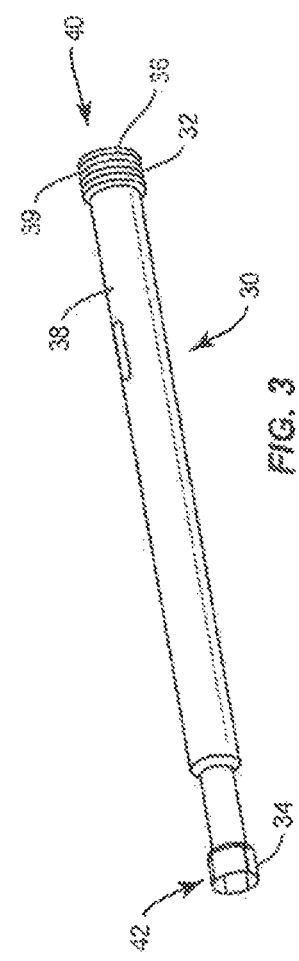
FIG. 3 is a perspective view of the components shown in FIG. 1.

The exemplary embodiments of a surgical system are discussed in terms of medical devices for the treatment of musculoskeletal disorders and more particularly, in terms of a surgical system and a method for treating a spine. In some embodiments, the system comprises a surgical instrument and related methods of use, which can be employed with spinal constructs including bone fasteners and connectors having a pop on, snap on, click on and/or slide on member that provides a universal connection system to spine surgeons. In some embodiments, the spinal construct allows the use of a singular bone screw component with multiple types of receivers thereby minimizing inventory while creating assemblies customized for a specific patient.

In some embodiments, the system comprises a surgical instrument and related methods of use, which can be employed with bone screw shanks that are not pre-coupled to a tulip head. In some embodiments, such bone screws without pre-coupled tulip heads allow for modular implant selection with minimal inventory in an operating room and an ability to provide a spinal rod receiver attachment in-situ.

In one embodiment, the system includes a surgical instrument, such as, for example, a bone screw driver configured to drive a bone screw shank without a tulip head. In one embodiment, the system includes a driver configured to provide a secure engagement to a bone screw that does not have a traditional tulip head or other type of spinal rod receiver member. In one embodiment, the system includes a driver having an inner sleeve with a flexible collet. In one embodiment, the system includes a driver having a flexible collet configured to snap around a spherical head of the bone screw by pushing an outer sleeve down that is configured to force the inner sleeve down. In one embodiment, the system includes a driver having inner and outer sleeves coupled together with a threaded interface and are configured for relative translation from a first open position to a second closed position.

In one embodiment, the system includes a driver having an outer sleeve configured to prevent a flexible collet from expanding in a closed position and allows disengagement from the bone screw in an open position. In one embodiment, the system includes a driver having an outer sleeve that is configured to apply a force to a retaining cap Of a driver shaft as the outer sleeve is translated. In one embodiment, the system includes a driver having an outer sleeve configured for translation to apply a compression force between a bone screw and a collet to secure the screw to the driver thereby reducing toggle between the bone screw and the driver shaft.

In one embodiment, the system includes a driver having a tip that simulates a shape of a tulip head and provides a hard stop preventing the bone screw from threading too far. In one embodiment, the system includes a driver having a tip that is a reamer configured to bore a path to allow a tulip head to be engaged without interference from a patient anatomy.

In one embodiment, the system includes a surgical instrument, such as, for example, a driver. In some embodiments, the driver has an outer sleeve having an outer sleeve tube. In some embodiments, the outer sleeve has a handle configured to rotate relative to the outer sleeve tube. In some embodiments, the driver has an inner sleeve and a driver shaft with an orientation pin. In some embodiments, the driver has a retainer cap. In one embodiment, the system includes a driver having a threaded handle configured to translate an outer sleeve and apply a compression force between a bone screw and an inner sleeve. In one embodiment, the system includes a driver having a reamer tip. In one embodiment, the system includes a driver having a collet on an inner sleeve configured to snap onto a sphere of a bone screw.

In one embodiment, the system includes a driver having a tip configured to simulate a tulip head and prevent a bone screw from being driven too deep into a patient anatomy to allow a tulip head attachment. In one embodiment, the driver has a collet on the inner sleeve.

In one embodiment, the system includes a driver that provides a secure and rigid connection between a bone screw without a tulip head or receiver component. In one embodiment, the system includes a driver that facilitates the use of implant systems in which a tulip head can be attached to the bone screw.

In one embodiment, the system includes an instrument having a collar that slides over a spherical head of a fastener. In one embodiment, the system includes an instrument having three sleeves. In one embodiment, the system includes an instrument having an internal shaft configured as a driver. In one embodiment, the system includes an instrument having a combination of two sleeves disposed around an outside of a driver. In one embodiment, the instrument includes a driver configured to extend beyond a sleeve such that an end of the driver extends past an end of the sleeve to the fastener. In one embodiment, the system includes an instrument having a sleeve configured to translate over a top of the fastener and rotated along a threaded engagement with a second sleeve for locking the instrument. In one embodiment, the system includes an instrument configured to prevent the fastener from penetrating too deep into tissue to allow an implant to be connected with the head of the fastener. In one embodiment, the system includes an instrument having an end tip of a sleeve configured to replicate a geometry of a fastener receiver to facilitate connection of the fastener receiver with the head of the fastener. In one embodiment, the system includes an instrument having a diameter at an end of an outer sleeve similar to a diameter of a tulip receiver for a fastener.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other steal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-9, there are illustrated components of a surgical implant system 10, in accordance with the principles of the present disclosure.

The components of system 10 can be fabricated from biologically acceptable materials suitable for medical applications, including metals, synthetic polymers, ceramics and bone material and/or their composites. For example, the components of system 10, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologic Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10, which includes surgical instrument 12, is employed, for example, with an open or mini-open, minimal access and/or minimally invasive including percutaneous surgical technique to deliver and fasten an implant at a surgical site within a body of a patient, for example, a section of a spine. In one embodiment, the components of system 10 are configured to fix a bone fastener with tissue for a surgical treatment to treat various spine pathologies, such as those described herein.

Figure 4:
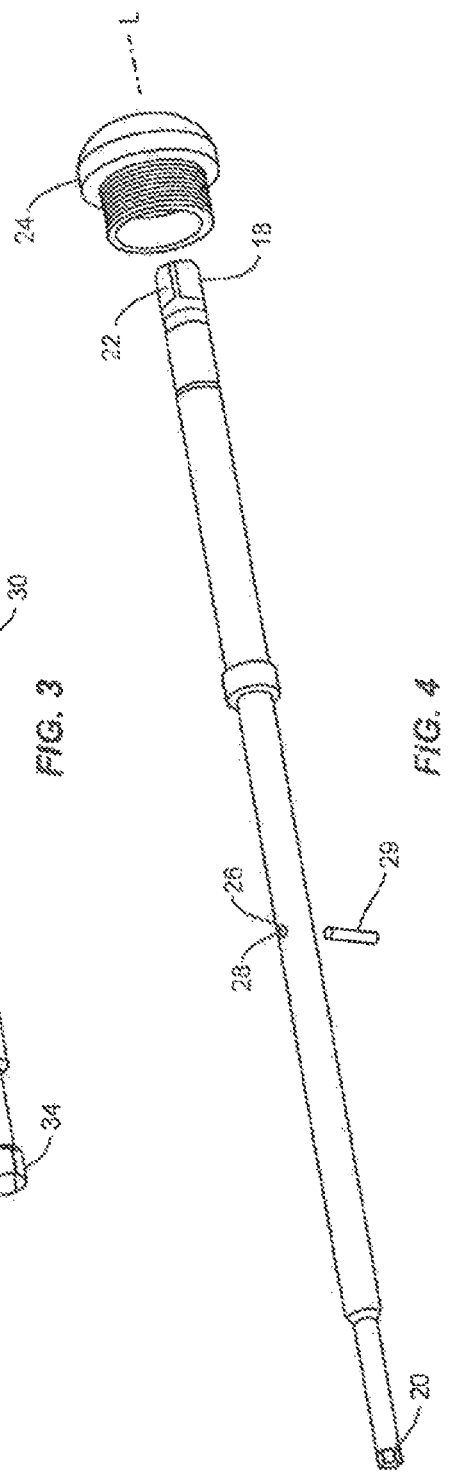
FIG. 4 is a perspective view of the components shown in FIG. 1.
Figure 4A:
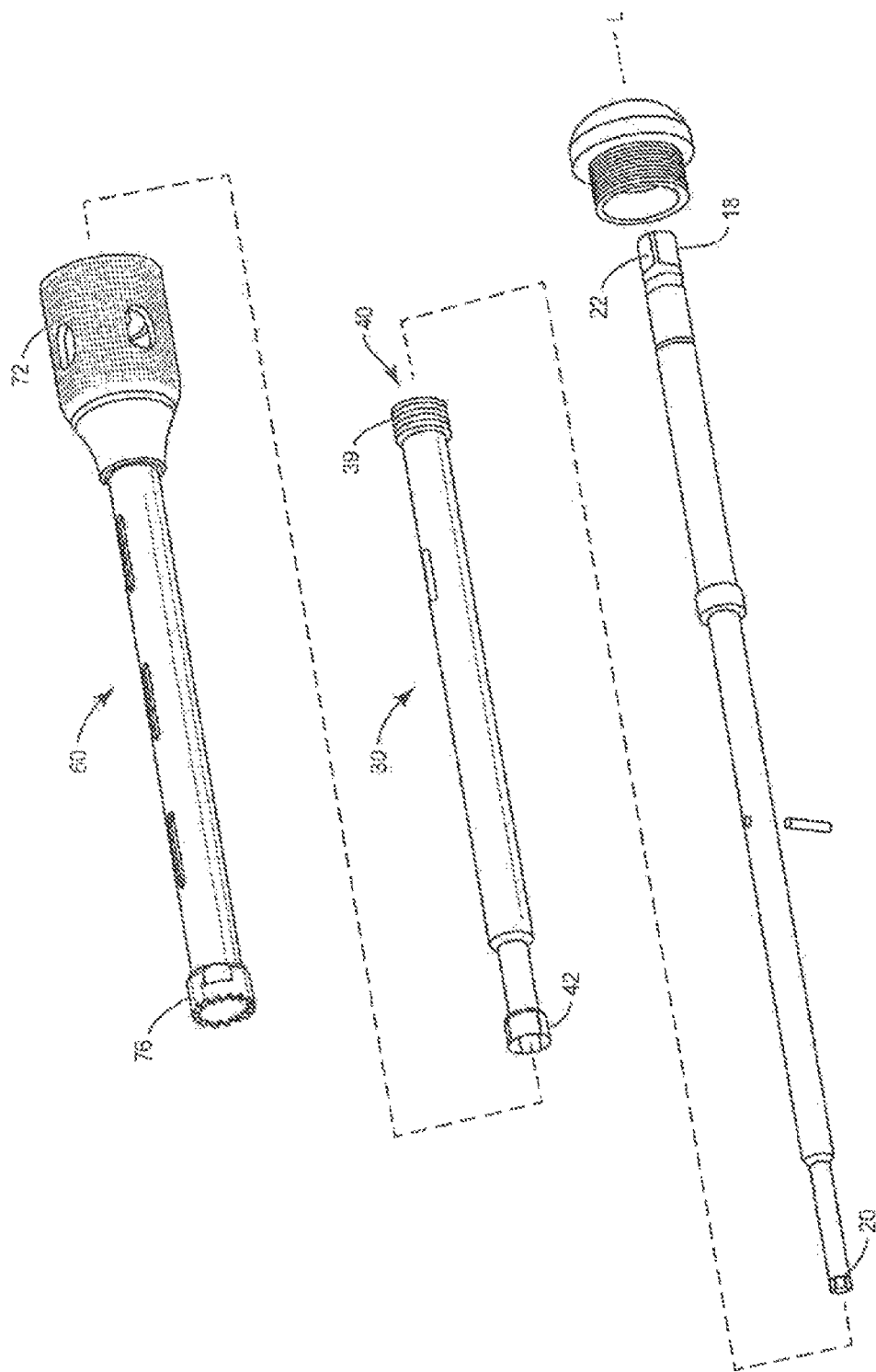
FIG. 4a is a break away view of the components shown in FIG. 1.
Figure 6:
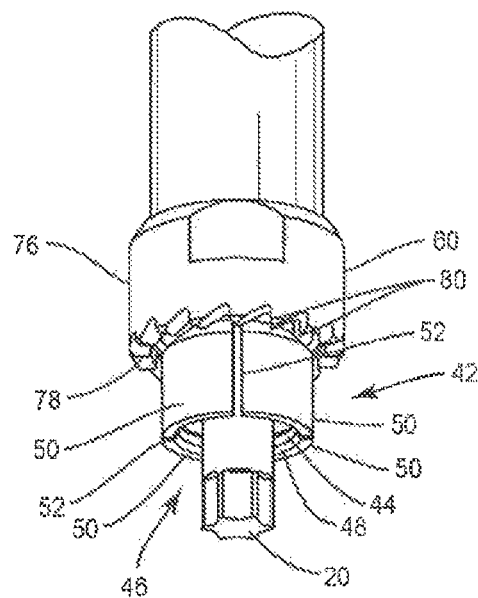
FIG. 6 is a break away view of components shown in FIG. 1.
Figure 7:
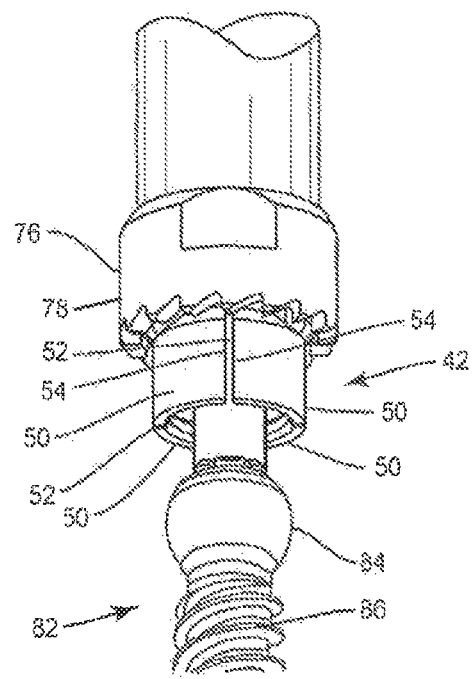
FIG. 7 is a break away view of components shown in FIG. 1.
Figure 8:
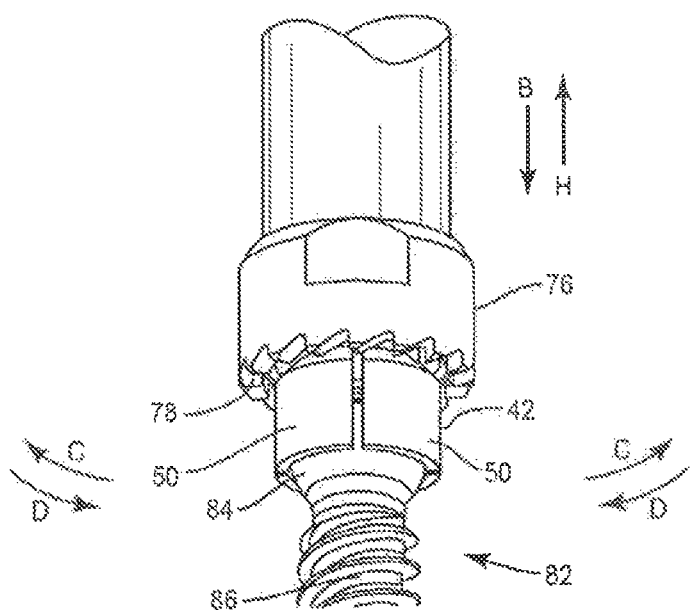
FIG. 8 is a break away view of components shown in FIG. 1.
Figure 9:
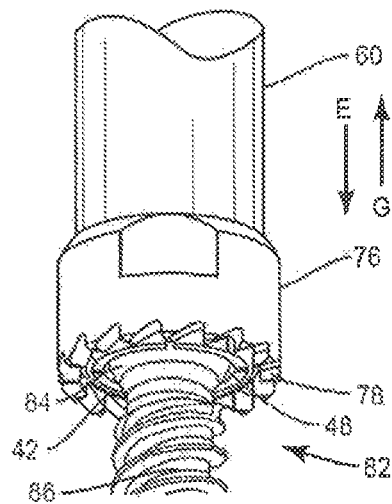
FIG. 9 is a break away view of components shown in FIG. 1.

System 10 includes surgical instrument 12, which includes a member, such as, for example, a driver shaft 14 extending along an axis L between an end 18 and an opposite end 20, as shown in FIGS. 4-5. End 18 includes a mating surface 22 configured to facilitate manipulation and/or maneuvering of surgical instrument 12. Surface 22 is configured for engagement with a retaining cap 24. In one embodiment, driver shaft 14 includes a surface 26 that defines a cavity 28 configured to receive an orientation pin 29.

End 20 is configured for engagement with an implant, such as, for example, a bone fastener 82, as shown in FIG. 5. In some embodiments, end 20 may have different cross-sections such as square, hexagonal, polygonal, triangular, star or hexalobe. End 20 may have various surface configurations, such as, for example, smooth, rough, arcuate, undulating, porous, semi-porous, dimpled, polished and/or textured.

A member, such as for example, a sleeve 30 is configured for disposal of driver shaft 14. Sleeve 30 extends between an end 32 and an end 34 along axis L. Sleeve 30 includes an inner surface 36 and an outer surface 38. Surface 36 defines a passageway 40 coaxial with axis L and configured for disposal of driver shaft 14. Surface 38 includes a threaded portion 39 configured for engagement with a third member, as described herein. End 34 includes an expandable member, such as, for example, a collet 42.

Collet 42 extends from end 34 and is configured for movement between a first configuration and a second configuration, as described herein. Collet 42 comprises an inner surface 44 defining a passageway 46, as shown in FIGS. 6-9. Passageway 46 is coaxial with passageway 40. Passageway 46 has a cylindrical cross-section configuration. In some embodiments, passageway 46 may have various cross section configurations, such as, for example, oval, oblong, triangular, rectangular, square, polygonal, irregular, uniform, non-uniform, variable, tubular and/or tapered.

Collet 42 includes a locking surface 48 defined by a plurality of cantilevered fingers 50 extending radially outward. Fingers 50 are circumferentially disposed and are equidistantly spaced apart. Fingers 50 are spaced apart by a gap 52 defined by opposite planar sidewalls 54. In one embodiment, collet 42 is flexible such that collet 42 is biased in the first, closed position, as described herein. Collet 42 is configured to snap fit around a first end, such as, for example, a head 84 of fastener 82. As collet 42 translates overhead 84 of fastener 82, collet 42 moves from a first closed position to a second open position and back to the first closed position to capture head 84.

System 10 includes a third member, such as, for example, a sleeve 60. Sleeve 60 extends between an end 62 and an end 64 along axis L. Sleeve 60 includes an inner surface 66 and an outer surface 68. Surface 66 defines a passageway 70 coaxial with axis L and configured for moveable disposal of sleeve 30. In one embodiment, inner surface 66 may have various surface configurations to enhance engagement of sleeve 30 and/or collet 42, such as, for example, rough, arcuate, undulating, porous, semi-porous, dimpled, polished and/or textured.

End 62 includes a handle 72 having a threaded inner surface 74 configured to rotatably engage threaded portion 39 for axial translation of sleeve 60 relative to sleeve 30, which causes releasable locking of collet 42 with bone fastener 82, as discussed herein. End 64 includes a tip 76 defining a reamer end surface 78. Reamer end surface 78 includes a plurality of teeth 80 configured to bore a path around head 84. In one or more cases, the teeth 80 are angled to cut in the direction of rotation of the reamer end surface 78. In one or more other cases, the teeth 80 may be angled to be bi-directional such that the teeth 80 may bore into tissue disposed about head 85 in a clockwise direction and/or a counter clockwise direction. In one or more cases, the teeth 80 are configured to spin independent of sleeve 60 such that they rotate independent to elongated shaft 86.

Sleeve 60 is configured to lock collet 42 with head 84, as discussed herein, for releasable fixation with bone fastener 82. Sleeve 60 extends along a portion of sleeve 30 and is configured for axial translation relative to sleeve 30. As sleeve 60 axially translates, in the direction shown in by arrow E in FIG. 9, fingers 50 are driven further inwardly by the force of sleeve 60 engaging collet 42 such that fingers 50 are moveable to the locked position around head 84 with locking surface 48.

System 10 includes a fastener, such as, for example, a bone fastener 82. Fastener 82 includes a head 84 configured for engagement with driver shaft 14 and an elongated shaft 86 configured for penetrating tissue. Head 84 comprises a spherical configuration. Head 84 includes an outer circumferential surface 88 having a substantially uniform diameter thereabout. In some embodiments, all or only a portion of surface 88 includes a spherical configuration. Head 84 includes an inner surface 90 that defines a cavity, such as, for example, a mating surface 92. Mating surface 92 is configured for disposal of an instrument and/or tool extension, such as, for example, end 20 of driver shaft 14, as discussed herein. Mating surface 92 is centrally positioned with respect to head 84. Mating surface 92 is coaxial with axis L. In some embodiments, mating surface 92 may have various cross-section configurations, such as, for example, oval, oblong, triangular, rectangular, square, polygonal, irregular, uniform, non-uniform, variable, tubular and/or tapered. In some embodiments, inner surface 90 may have various surface configurations, such as, for example, smooth and/or surface configurations to enhance engagement with the mating surface of driver shaft 14, such as, for example, rough, arcuate, undulating, porous, semi-porous, dimpled, polished and/or textured.

Shaft 86 has a cylindrical cross section configuration and includes an outer surface having an external thread form. In some embodiments, the thread form may include a single thread turn or a plurality of discrete threads. In some embodiments, other engaging structures may be disposed on shaft 86, such as, for example, a nail configuration, barbs, expanding elements, raised elements and/or spikes to facilitate engagement of shaft 86 with tissue, such as, for example, vertebrae.

In some embodiments, all or only a portion of shaft 86 may have alternate cross section configurations, such as, for example, oval, oblong, triangular, square, polygonal, irregular, uniform, non-uniform, offset, staggered, undulating, arcuate, variable and/or tapered. In some embodiments, the outer surface may include one or a plurality of openings. In some embodiments, all or only a portion of the outer surface may have alternate surface configurations to enhance fixation with tissue such as, for example, rough, arcuate, undulating, mesh, porous, semi-porous, dimpled and/or textured. In some embodiments, all or only a portion of shaft 86 may be disposed at alternate orientations, relative to a longitudinal axis of bone fastener 82, such as, for example, transverse, perpendicular and/or other angular orientations such as acute or obtuse, co-axial and/or may be offset or staggered. In some embodiments, all or only a portion of shaft 86 may be cannulated.

In assembly, operation and use, a surgical implant system 10, similar to the systems and methods described herein, is employed with a surgical procedure for treatment of a spinal disorder affecting a section of a spine of a patient, as discussed herein. For example, system 10 can be used with a surgical procedure for treatment of a condition or injury of an affected section of the spine including vertebrae. In some embodiments, one or all of the components of system 10 can be delivered as a pre-assembled device or can be assembled in situ. System 10 may be completely or partially revised, removed or replaced.

For example, system 10 can be employed with a surgical treatment of an applicable condition or injury of an affected section of a spinal column and adjacent areas within a body, such as, for example, vertebrae (not shown). In some embodiments, system 10 may be employed with one or a plurality of vertebra. To treat a selected section of the vertebrae, a medical practitioner obtains access to a surgical site including the vertebrae in any appropriate manner, such as through incision and retraction of tissues. In some embodiments, system 10 can be used in any existing surgical method or technique including open surgery, mini-open surgery, minimally invasive surgery including percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of implantable components of system 10. A preparation instrument (not shown) can be employed to prepare tissue surfaces of vertebrae, as well as for aspiration and irrigation of a surgical region.

Surgical instrument 12 is disposable in a first position such that collet 42 is in a biased closed position extending a distance from end 64 of sleeve 60. End 20 of driver shaft 14 is engaged with mating surface 92. Rotation of handle 72, in the direction shown by arrow A in FIG. 5, causes sleeve 30 to translate along axis L, in the direction shown by arrow B in FIG. 8, to cause collet 42 to capture head 84. Fingers 50 of collet 42 expand, in the direction shown by arrow C in FIG. 8, into a second position as fingers 50 translate over surface 88. As fingers 50 translate over surface 88, fingers 50 are urged due to the resilient bias of fingers 50 into the first position, by moving in the direction shown by arrow D in FIG. 8, to snap fit around head 84 to capture head 84 within fingers 50. Locking surface 48 is in contact with surface 88. Further rotation of handle 72 causes sleeve 60 to translate, in the direction shown by arrow E in FIG. 9, such that end 76 of sleeve 60 translates over collet 42 and compresses fingers 50 of collet 42 and tighten fingers 50 about surface 88 of head 84 to releasably fix surgical instrument 12 with fastener 82.

Translation of sleeve 60 causes' teeth 80 of reamer end surface 78 to bore into tissue disposed about head 85. In some embodiments, reamer end surface 78 creates a circumferential pathway around head 84 providing space for an implant, such as, for example, a spinal rod receiver to be connected with head 84.

Driver shaft 14 is rotated to apply a torsional force to bone screw 82 and increase the depth of the pilot hole and/or fasten bone screw 82 with tissue. As the depth of the pilot whole increases, shaft 86 engages the outer layer of cortical bone such that further rotation of bone screw 82 about axis L causes shaft 86 to move through the pilot hole and the outer layer of cortical bone and into a layer of cancellous bone. In some embodiments, bone screw 82 is rotated until the shaft of bone screw 82 penetrates the vertebra to fix bone screw 82 with the tissue.

The components of system 10, including surgical instrument 12 and bone screw 82, are employed to augment one or more surgical treatments. Surgical instrument 12 is disposable in the first, non-locking orientation, as described herein, to release bone screw 182 from collet 60. To disengage instrument 12 from fastener 82, handle 72 is rotated in the opposite direction, shown by arrow F in FIG. 5, to translate sleeve 60, in the direction shown by arrow G, to release the compression force about collet 42. Rotation of handle 72 causes sleeve 30 to translate, in the direction shown by arrow H in FIG. 8, to translate fingers 50 away from head 84 to disengage fingers 50 from head 84. End 20 of driver shaft 14 is disengaged from mating surface 92.

Surgical instrument 12 may be re-assembled for use in a surgical procedure. In some embodiments, system 10 may comprise various instruments including a lock and collet configuration of the present disclosure, with, for example, inserters, extenders, reducers, spreaders, distractors, blades, retractors, clamps, forceps, elevators and drills, which may be alternately sized and dimensioned, and arranged as a kit.

Upon completion of a procedure, surgical instrument 12, surgical instruments and/or tools, assemblies and non-implanted components of system 10 are removed and the incision(s) are closed. One or more of the components of system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 10. In some embodiments, system 10 may include one or a plurality of plates, connectors and/or bone fasteners for use with a single vertebral level or a plurality of vertebral levels.

In one embodiment, as shown in FIGS. 10-15, spinal implant system 10, similar to the systems and methods described herein, comprises instrument 12 described herein, having driver shaft 14, sleeve 30 and a sleeve 160, similar to sleeve 60, described herein. Driver shaft 14 extends along an axis L between an end 18 and an opposite end 20.

Figure 12:
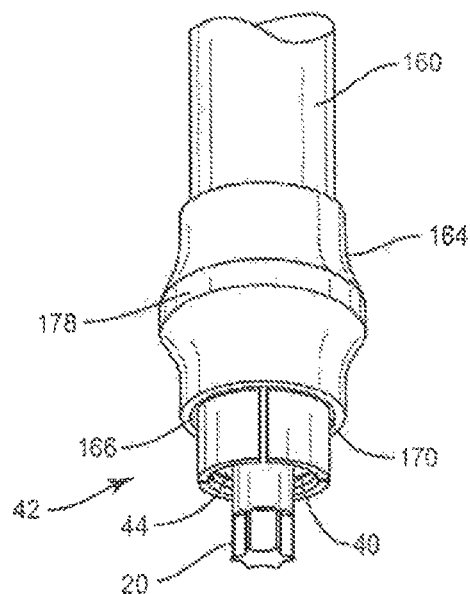
FIG. 12 is a break away view of components shown in FIG. 10.
Figure 13:
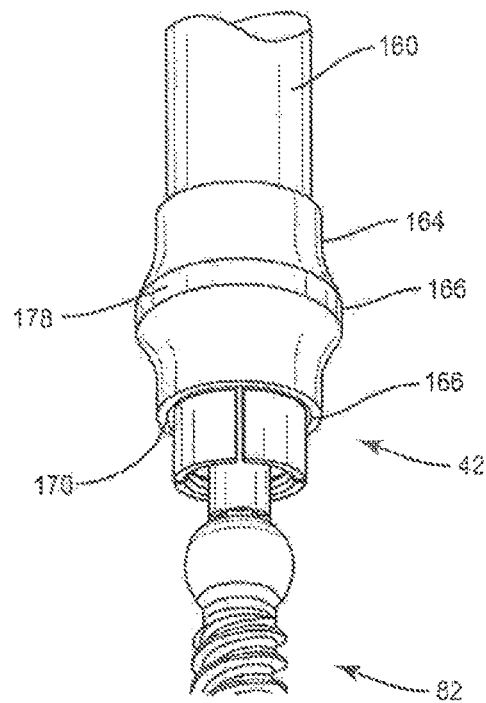
FIG. 13 is a break away view of components shown in FIG. 10.
Figure 14:
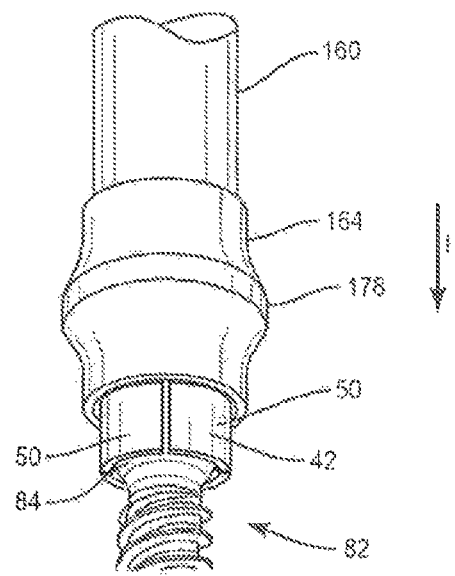
FIG. 14 is a break away view of components shown in FIG. 10.
Figure 15:
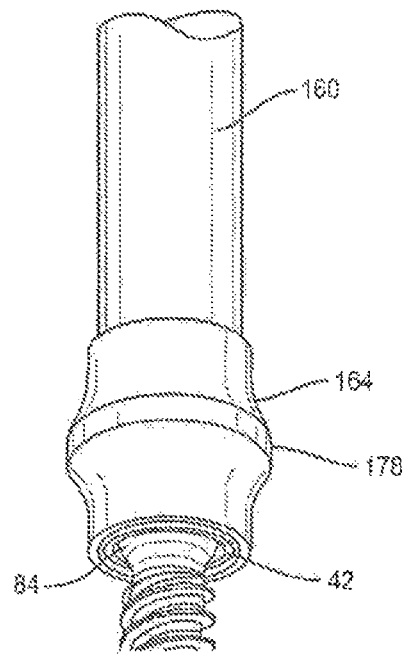
FIG. 15 is an end view of components of the surgical system shown in FIG. 10.

End 20 is configured for engagement with bone fastener 82, as shown in FIG. 10. Sleeve 30 is configured for disposal of driver shaft 14. Sleeve 30 extends along axis L. Sleeve 30 includes a passageway 40 coaxial with axis L and configured for disposal of driver shaft 14. Sleeve 30 includes collet 42, as described herein. Collet 42 is configured for movement between a first configuration and a second configuration, as described herein. Collet 42 comprises an inner surface 44 defining a passageway 46, as shown in FIGS. 12-13. Passageway 46 is coaxial with passageway 40.

Sleeve 160 extends between an end 162 and an end 164 along axis Sleeve 160 includes an inner surface 166 and an outer surface 168. Surface 166 defines a passageway 170 coaxial with axis L and configured for moveable disposal of sleeve 30.

End 162 includes a handle 172 having a threaded inner surface (not shown), similar to threaded surface 74. The threaded surface is configured to rotatably engage threaded portion 39 for axial translation of sleeve 160 relative to sleeve 30, which causes releasable locking of collet 42 with bone fastener 82, as discussed herein. End 164 is dimensioned and/or configured similar to a tulip head receiver, as shown in FIG. 12. End 164 includes a diameter similar to a diameter of a tulip head receiver. End 164 defines a cavity configured to receive collet 42 and head 84 such that end 164 is disposed about head 84 and collet 42 such that there is space disposed about head 84 for connection of a receiver.

Sleeve 160 is configured to lock collet 42 with head 84, as discussed herein, for releasable fixation with bone fastener 82. Sleeve 160 extends along a portion of sleeve 30 and is configured for axial translation relative to sleeve 30. As sleeve 60 axially translates, in the direction shown by arrow I in FIG. 14, fingers 50 are driven inwardly by the force of sleeve 160 engaging collet 42 such that fingers 50 are moveable to the locked position about head 84 with locking surface 48.

End 164 includes a hard stop portion 178 configured to prevent fastener 82 from penetrating into tissue beyond a selected limit. Hard stop portion 178 allows for connection of a receiver with head 84.

In one embodiment, as shown in FIGS. 16-21C, surgical implant system 200 includes one or more of the same or similar features as described herein with respect to system 10. The components of system 200 can be fabricated and/or formed using one or more of the materials described with respect to system 10. Accordingly, a description of these materials is not repeated.

System 200, which includes surgical instrument 210, is employed, for example, with an open or mini-open, minimal access and/or minimally invasive including percutaneous surgical technique to deliver and fasten an implant at a surgical site within a body, for example, a section of a spine of a patient. In one embodiment, the components of system 200 are configured to fix a bone fastener, such as bone fastener 222, for a surgical treatment to treat various spine pathologies, such as those described herein.

Figure 18A:
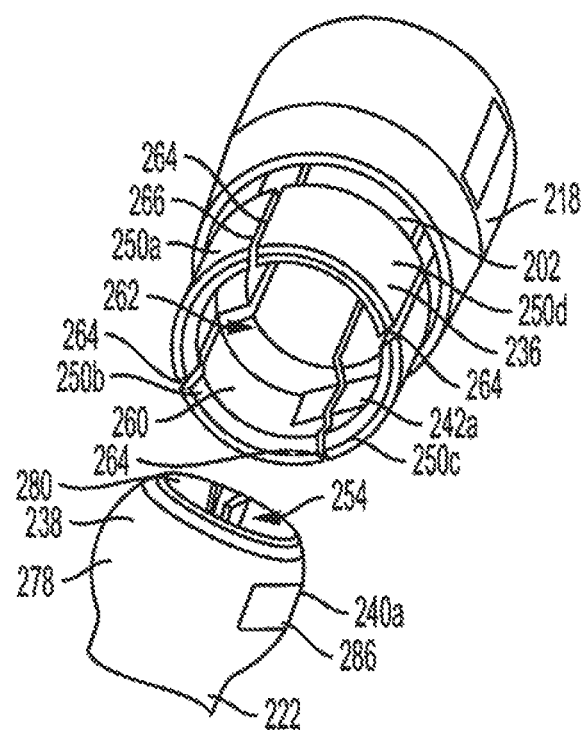
FIG. 18A is a perspective view of components of the surgical system shown in FIG. 16.
Figure 18B:
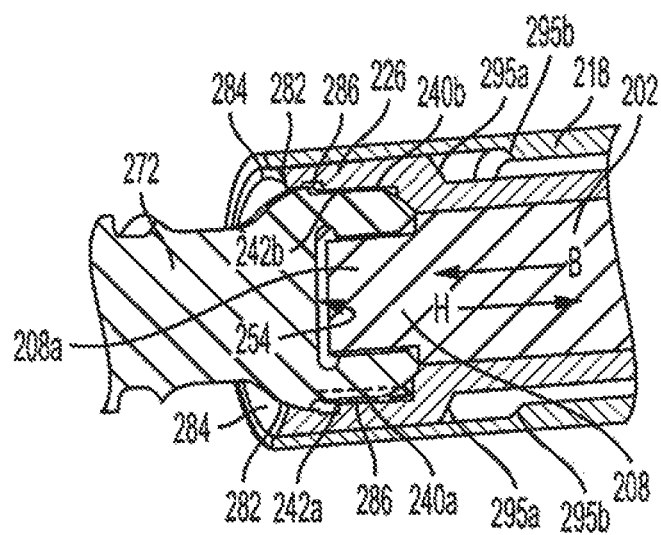
FIG. 18B is a cross-section view of components of the surgical system shown in FIG. 16.

System 200 includes a fastener, such as, for example, a bone fastener 222, as shown in FIGS. 18A and 18B. Fastener 222 includes a head 238 configured for engagement with driver shaft 202 and an elongated shaft 252 configured for penetrating tissue. Head 238 comprises a spherical configuration. Head 238 includes an outer circumferential surface 278 having a substantially uniform diameter thereabout. In some embodiments, all or only a portion of surface 278 includes a spherical configuration. Head 238 includes an inner surface 280 that defines a cavity, such as, for example, a mating surface 254. Mating surface 254 is configured for disposal of an instrument and/or tool extension, such as, for example, a mating surface 208a on an end 208 of driver shaft 202, as discussed herein. Mating surface 254 is centrally positioned with respect to head 238. Mating surface 254 is coaxial with axis Li. In some embodiments, mating surface 254 may have various cross-section configurations, such as, for example, oval, oblong, triangular, rectangular, square, polygonal, irregular, uniform, non-uniform, variable, tubular and/or tapered. In some embodiments, inner surface 280 may have various surface configurations, such as, for example, smooth and/or surface configurations to enhance engagement with the mating surface 208a of driver shaft 202, such as, for example, rough, arcuate, undulating, porous, semi-porous, dimpled, polished and/or textured.

Shaft 252 of the fastener 222 has a cylindrical cross section configuration and includes an outer surface having an external thread form. In some embodiments, the thread form may include a single thread turn or a plurality of discrete threads. In some embodiments, other engaging structures may be disposed on shaft 252, such as, for example, a nail configuration, barbs, expanding elements, raised elements and/or spikes to facilitate engagement of shaft 252 with tissue, such as, for example, vertebrae.

In some embodiments, all or only a portion of shaft 252 may have alternate cross section configurations, such as, for example, oval, oblong, triangular, square, polygonal, irregular, uniform, non-uniform, offset, staggered, undulating, arcuate, variable and/or tapered. In some embodiments, the outer surface may include one or a plurality of openings. In some embodiments, all or only a portion of the outer surface may have alternate surface configurations to enhance fixation with tissue such as, for example, rough, arcuate, undulating, mesh, porous, semi-porous, dimpled and/or textured. In some embodiments, all or only a portion of shaft 252 may be disposed at alternate orientations, relative to a longitudinal axis Li of bone fastener 222, such as, for example, transverse, perpendicular and/or other angular orientations such as acute or obtuse, co-axial and/or may be offset or staggered. In some embodiments, all or only a portion of shaft 252 may be cannulated.

In one or more embodiments, the outer circumferential surface 278 of the head 238 includes one or more screw flats, such as screw flat 240a and screw flat 240b. The screw flat 240a may be configured in a geometry that mates with a key portion, such as key portion 242a and 242b, of a collet 236, as discussed herein. In one or more cases, the keyed surface 286 of the screw flat 240a may be notched into the outer circumferential surface 278 of the head 238. In one or more other cases, the key surface 286 of the screw flat 240a may protrude from the outer circumferential surface 278 of the head 238. The keyed surface 286 of the screw flat 240a may have a flat shape. The keyed surface 286 of the screw flat 240a may extend across the outer circumferential surface 278 of the head 238. It is noted that the screw flat 240b includes one or more of the same or similar features as screw flat 240a. Accordingly, a description of such features for screw flat 240b is not repeated. It is also noted that two screw flats are described; however, embodiments are contemplated in which the head 238 includes one screw flat and in which the head 238 includes greater than two screw flats, for example, four screw flats, in which the collet 236 includes a corresponding number of key portions, such as, four key portions.

Figure 16:
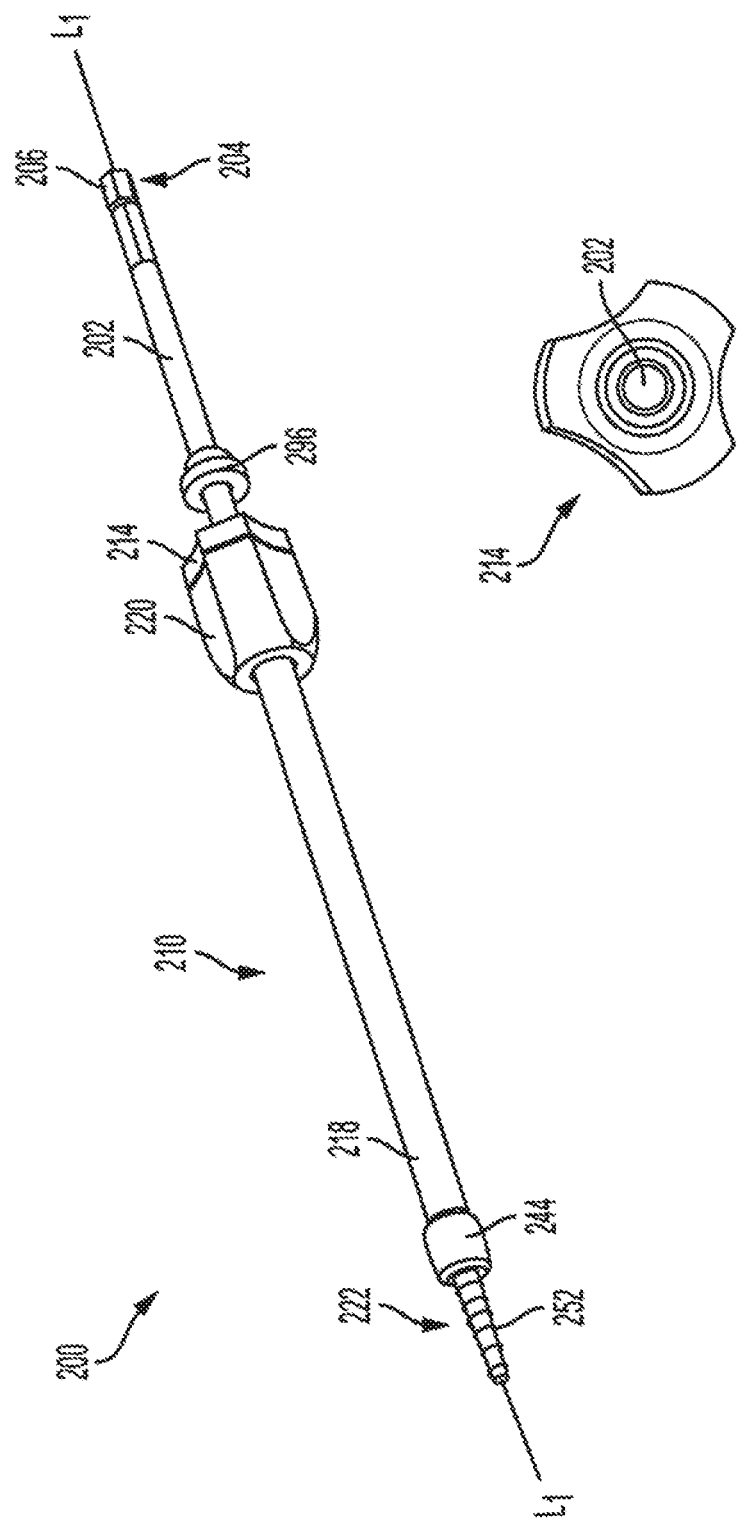
FIG. 16 is a perspective view of components of a surgical system in accordance with the principles of the present disclosure.
Figure 17:
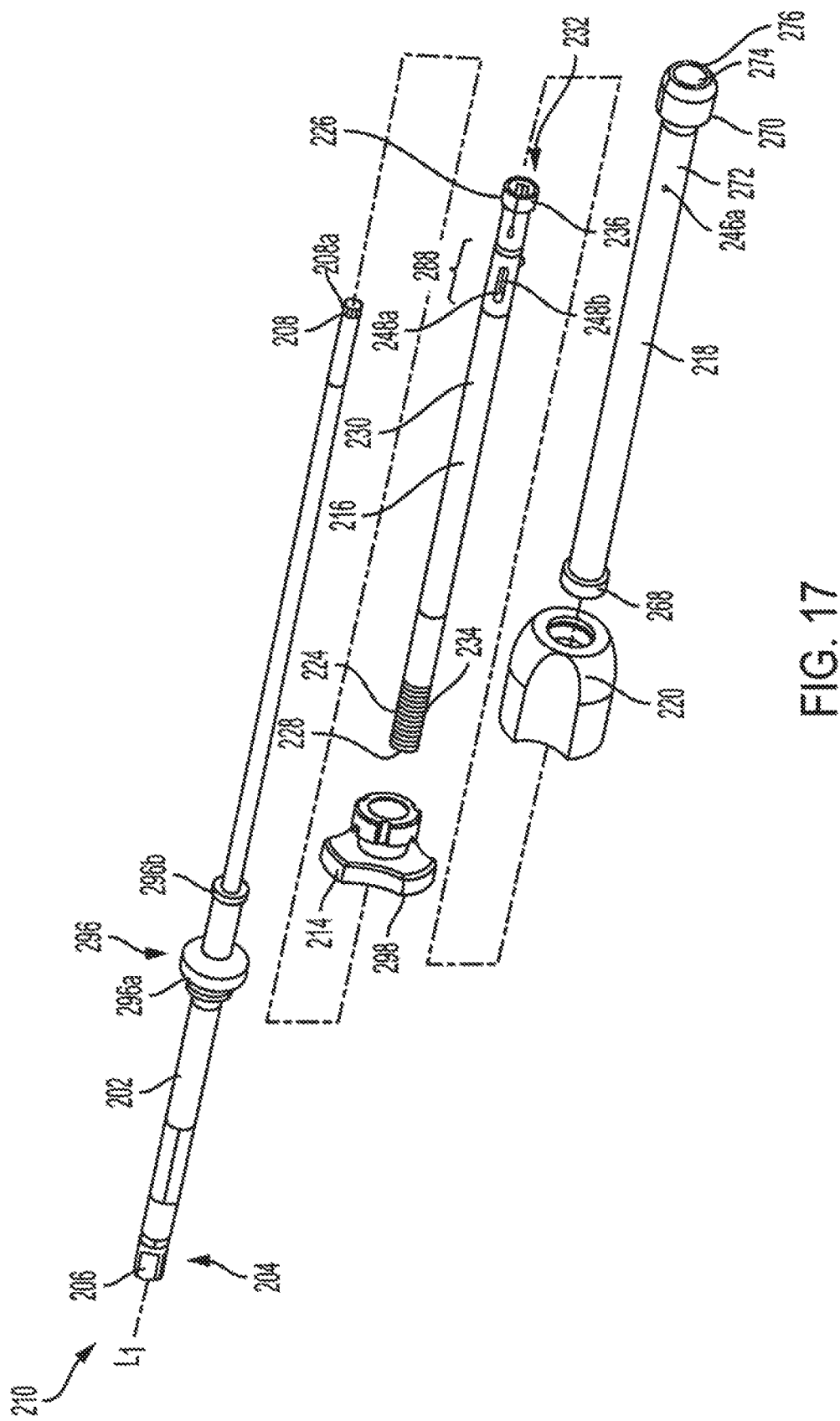
FIG. 17 is a break away view of the components shown in FIG. 16.

System 200 includes surgical instrument 210, which includes a member, such as, for example, a driver shaft 202 extending along an axis Li between an end 204 and an opposite end 208, as shown in FIGS. 16-17. The end 204 includes a mating surface 206 configured to facilitate manipulation and/or maneuvering of the surgical instrument 210. The surface 206 is configured for engagement with a handle. The handle may have a receiving portion on an inner surface of the handle, in which the surfaces of the receiving portion are configured to receive the end 204 of the driver shaft 202.

The driver shaft 202 may be an elongated rigid member having a solid center. The driver shaft 202 may include a stopper 296 disposed around the outer surface of the shaft 202. The stopper 296 may be a rigid body having a bushing 296a positioned on one end of the stopper 296 and protrudes outwards from the shaft 202. The stopper 296 may have a cylindrical disk 296b positioned on an end of the stopper 296 opposite the bushing 296a.

Figure 20A:
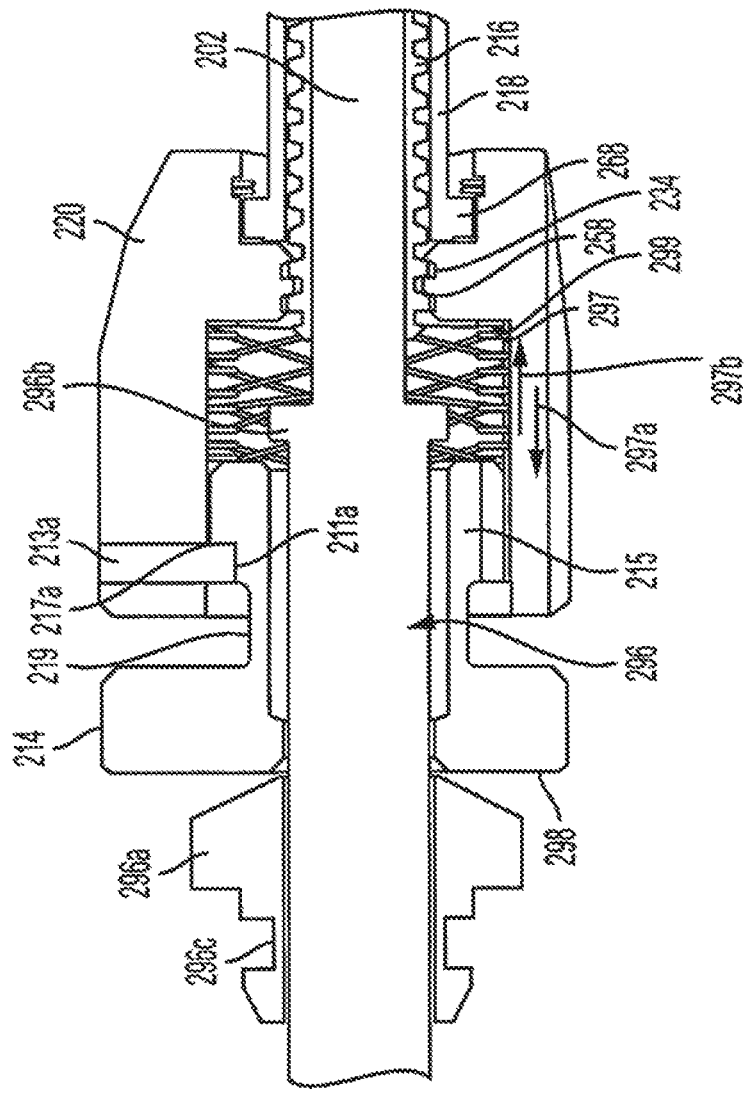
FIG. 20A is a cross-section view of components shown in FIG. 16.

The bushing 296a and the cylindrical disk 296b may be positioned on the shaft 202 a set distance away from one another to prevent the shaft 202 from translating through sleeves 216 and 218 beyond the set distance. For example, the bushing 296a may contact an outer surface 298 of the knob 214 and may prevent the driver shaft 202 from moving a set distance towards the end 270. In another example, the cylindrical disk 296b may contact an inner surface of the knob 214 and prevent the driver shaft 202 from moving a set distance away from the end 270. In one or more cases, the knob 214 can rotate about the driver shaft 202 and can translate over the driver shaft 202 relative to the distance defined by the bushing 296a and the cylindrical disk 296b. In one or more cases, the bushing 296a may be used to facilitate connecting the surgical instrument 210 with a navigation tracking instrument, such as a NavLock™ Tracker available from Medtronic, Inc. The navigation tracking instrument may be coupled to the groove portion 296c of the bushing 296a, as shown in FIG. 20A.

The mating surface 208a on the end 208, as shown in FIG. 16, is configured for engagement with an implant, such as, for example, a bone fastener 222. In some embodiments, the end 208 may be formed with different cross-sectional shapes, such as, but not limited to, a square, hexagonal, polygonal, triangular, star, or, or preferably a hexalobe. The mating surface 208a may have various surface configurations, such as, for example, smooth, rough, arcuate, undulating, porous, semi-porous, dimpled, polished and/or textured. The mating surface 208a may be formed in a shape capable of being inserted in a mating surface 254 of the fastener 222.

The driver shaft 202 may be inserted through a passageway 232 of a member, such as for example, a sleeve 216. The sleeve 216 may be configured for disposal of driver shaft 202. The sleeve 216 may be an elongated tubular member having a cannulated center forming the passageway 232. The sleeve 216 extends between an end 224 and an end 226 along axis Li. The sleeve 216 includes an inner surface 228 and an outer surface 230. The surface 228 defines a passageway 232 coaxial with axis Li and configured for disposal of the driver shaft 202. The surface 230 includes a threaded portion 234 configured for engagement with a third member, such as a sleeve 218 and preferably a knob 220 of the sleeve 218. The end 226 includes an expandable member, such as, for example, a collet 236.

The collet 236 extends from the end 226 and is configured for movement between an open position and a closed position, as described herein. The collet 236 comprises an inner surface 260 defining a passageway 262, as shown in FIGS. 18A-18B. The passageway 262 is coaxial with the passageway 232. The passageway 262 has a cylindrical cross-section configuration. In some embodiments, the passageway 262 may have various cross-section configurations, such as, for example, oval, oblong, triangular, rectangular, square, polygonal, irregular, uniform, non-uniform, variable, tubular and/or tapered.

The collet 236 may be configured to snap fit around a head 238 of the fastener 222. As the collet 236 translates over the head 238 of fastener 222, the collet 236 moves from the closed position to the open position and back to the closed position to capture the head 238. The collet 236 may snap fit around the head 238 of the fastener 222 via a plurality of cantilevered fingers 250a, 250b, 250c, and 250d. The plurality of cantilevered fingers 250a, 250b, 250c, and 250d may define the inner surface 260, serving as a locking surface, of the collet 236. The fingers 250a, 250b, 250c, and 250d may extend radially outward from the end 226 of the sleeve 216. The fingers 250a, 250b, 250c, and 250d may be circumferentially disposed and are equidistantly spaced apart. The fingers 250a, 250b, 250c, and 250d are spaced apart by a gap 264 defined by opposite planar sidewalls 266. The distal end of the fingers 250a, 250b, 250c, and 250d may include a first surface 284 configured to engage the outer circumferential surface 278 of the head 238. The first surface 284 may taper towards the distal end of the fingers 250a, 250b, 250c, and 250d. The distal end of the fingers 250a, 250b, 250c, and 250d may include a second surface 282 integrally connected with the first surface 284. The second surface may taper away from the distal end of the fingers 250a, 250b, 250c, and 250d. It is noted that the collet 236 is described as having four fingers; however, embodiments are contemplated in which the collet 236 includes fewer than four fingers and in which the collet 236 includes greater than four fingers.

In one embodiment, the collet 236 is flexible such that the fingers 250a, 250b, 250c, and 250d are configured to move from the closed position to the open position and from the open position to the closed position. FIG. 18A illustrates the collet 236 biased in the closed position. FIG. 18B illustrates the collet 236 fitted around the head 238 of the fastener 222 in the first closed position. In the closed position, the fingers 250a, 250b, 250c, and 250d may be cantilevered from the end 226 of the sleeve 216, such that fingers 250a, 250b, 250c, and 250d extend parallel or substantially parallel with the inner surface 228 and/or outer surface 230 of the sleeve 216. In the open position, the fingers 250a, 250b, 250c, and 250d may flex outwards away from the center of the passageway 232.

In an example, the collet 236 may be biased in the closed position. In one or more cases, a user may insert the mating surface 208a of the driver shaft 202 into the mating surface 254 of the fastener 222. Subsequently, the user may begin to position the head 238 of the fastener 222 within the collet 236 of sleeve 216. As the collet 236 translates over the head 238 of the fastener 222, the first surface 284 of one or more of the fingers 250a, 250b, 250c, and 250d contacts the outer circumferential surface 278 of the head 238 and flexes outwards, in the direction C as shown in FIG. 21B, away from the center of the passageway 232, thereby moving the collet 236 into the open position. The tapered portion of the first surface 284 may facilitate translation of the fingers 250a, 250b, 250c, and 250d of the head 238. Having passed the first surface 284, the outer circumferential surface 278 of the head 238 contacts the second surface 282 of one or more of the fingers 250a, 250b, 250c, and 250d. As the second surface 282 translates over the head 238, the fingers 250a, 250b, 250c, and 250d flex inwards, in the direction D as shown in FIG. 21B, towards the center of the passageway 232, thereby returning the collet 236 to the closed position and coupling the fastener 222 to the instrument 210.

In one or more embodiments, one or more of the fingers 250a, 250b, 250c, and 250d includes a key portion, such as key portion 242a and key portion 242b. The key portion 242a may be configured in a geometry that mates with a screw flat 240a of the fastener 222. The collet 236 may include a number of key portions equal to the number of screw flats of the fastener 222. The key portion 242a may include a surface extending across the inner surface 260 of the collet 236. In one or more cases, the surface of the key portion 242a may be raised from the inner surface 260 of the collet 236 forming a notch. The raised surface of the key portion 242a may be configured to engage a keyed surface 286 of the screw flat 240a for the cases in which the keyed surface 286 of the screw flat 240a is notched. In one or more other cases, the surface of the key portion 242a may be a surface indented into the inner surface 260 of the collet 236 forming a cavity. The indented surface of the key portion 242a may be configured to engage the keyed surface 286 of the screw flat 240a for the cases in which the keyed surface 286 protrudes from the outer circumferential surface 278 of the head 238. The surface of the key portion 242a may be of a different shape, such as, for example, a flat shape, than the inner surface 260 of the collet 236. In one or more cases, the key portion 242a may be disposed entirely on one of the fingers 250a, 250b, 250c, and 250d. In one or more other cases, a portion of the key portion 242a may be disposed on a portion of one finger, such as finger 250b, and another portion of the key portion 242a may be disposed on a portion of an adjacent finger, such as 250c, as shown in FIG. 18A.

It is noted that the key portion 242b includes one or more of the same or similar features as key portion 242a. Accordingly, a description of such features for key portion 242b is not repeated. It is also noted that two key portions are described; however, embodiments are contemplated in which the collet 236 includes one key portion and in which the collet 236 includes greater than two key portions.

System 200 includes a third member, such as, for example, a sleeve 218, as shown in FIG. 17. The sleeve 218 extends between an end 268 and an end 270 along axis Li. The sleeve 218 includes an inner surface 274 and an outer surface 272. The inner surface 274 defines a passageway 276 coaxial with axis Li and is configured for moveable disposal of the sleeve 216. In one embodiment, the inner surface 274 may have various surface configurations to enhance engagement of the sleeve 216 and/or the collet 236, such as, for example, rough, arcuate, undulating, porous, semi-porous, dimpled, polished and/or textured.

Figure 19:
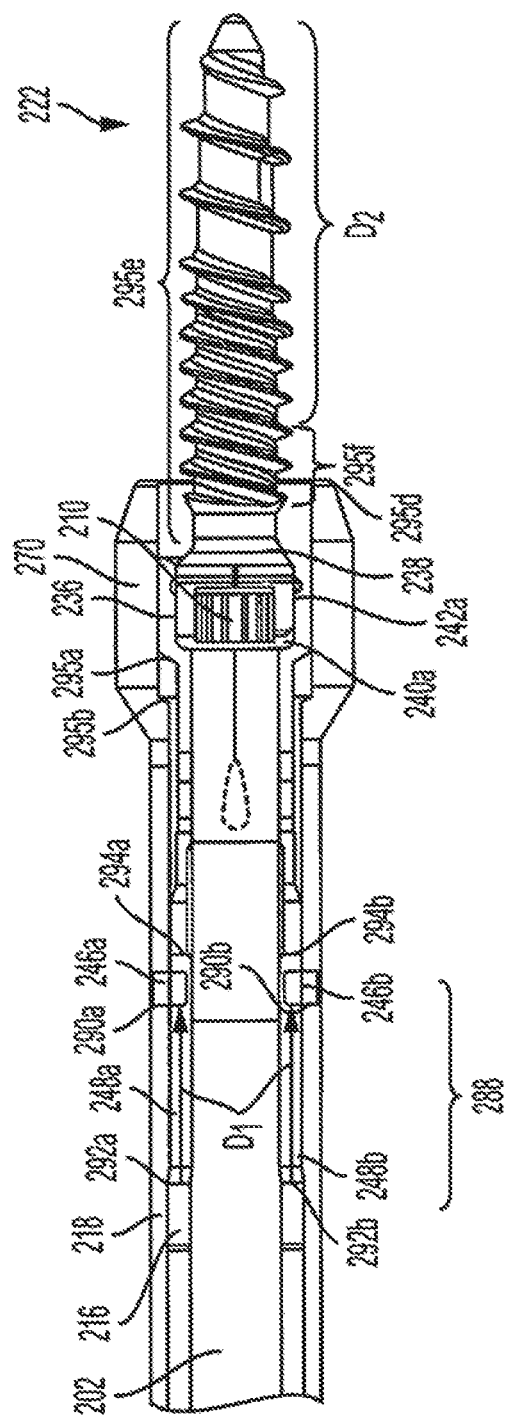
FIG. 19 is a cross-section view of components shown in FIG. 16.

The surgical instrument 210 may include a translation stop 288, as shown in FIG. 19. The translation stop 288 may be configured to limit the distance, for example a distance $D_1$, the sleeve 216 axially translates through the sleeve 218. Moreover, the translation stop 288 may be configured to prevent the sleeve 216 from axially rotating within the sleeve 218. The translation stop 288 may include one or more tracks, such as track 248a and track 248b, and one or more pins, such as pin 246a and 246b. In one or more cases, the track 248a and the track 248b may each be disposed on the sleeve 216 and the pin 246a and the pin 246b may each be disposed on the sleeve 218, as shown in FIGS. 17 and 19.

In one or more other cases, the track 248a and the track 248b may be disposed on the sleeve 218 and the pin 246a and the pin 246b may be disposed on the sleeve 216.

For the cases in which tracks 248a and 248b are disposed on the sleeve 216, the tracks 248a and 248b may be through-holes extending from the outer surface 230 of the sleeve 216 to the inner surface 228 of the sleeve 216. The tracks 248a and 248b may be sized to receive the pins 246a and 246b, respectively. For the cases in which pins 246a and 246b are disposed on the sleeve 218, the pins 246a and 246b may protrude into the passageway 276. The pins 246a and 246b may be disposed on the sleeve 218 such that the pins 246a and 246b may be positioned within the tracks 248a and 248b, respectively. The pins 246a and 246b may protrude far enough into the passageway 276 to contact at least a portion of the stopping surface 292a of track 248a and the stopping surface 292b of the track 248b. The pins 246a and 246b may protrude far enough into the passageway 276 to contact at least a portion of the stopping surface 294a of track 248a and the stopping surface 294b of the track 248b. The pins 246a and 246b may protrude far enough into the passageway 276 to not interfere with the driver shaft 202 moving within the passageway 232.

In one or more cases, the pins 246a and 246b and the stopping surfaces 292a and 292b are configured to prevent the sleeve 216 from moving beyond a set distance $D_1$. For example, as the sleeve 216 translates through the sleeve 218, the sleeve 216 may move the distance $D_1$ towards the distal end of the surgical instrument 210. Having moved the distance $D_1$, the stopping surfaces 292a and 292b contact the pins 246a and 246b, respectively, thereby limiting the distance the sleeve 216 axially translates through the sleeve 218.

In one or more cases, the end 270 of the sleeve 218 may act as a depth stop to prevent the fastener 222 from penetrating into a body, for example, a vertebral body of a spine, beyond a distance $D_2$. In one or more cases, the distance $D_2$ may range from at or about 3.5 millimeters (mm) to at or about 5 mm. More preferably, the distance $D_2$ may be at or about 4 mm. The end 270 of the sleeve 280 may be configured to surround a proximal thread 295f of the fastener 222. In one or more cases, by surrounding a portion of the thread 295f, as the fastener 222 is being fastened into, for example, a vertebral body and the collet 236 is retracted within the end 270, the outer surface 295d of the end 270 may contact an outer surface of the vertebral body, thereby preventing the fastener 22 from penetrating into the vertebral body any farther. That is, when the outer surface 295d of the end 270 of the sleeve 218 contacts the outer surface of the vertebral body, the surgical instrument 210 is prevented from inserting the full insertion depth 295e of the fastener 222 into the vertebral body. In one or more cases, the distance between the outer surface 295a of the collet 236 and the inner surface 295b of the end 270 of the sleeve 218 may define the length of the proximal thread 295f that can be surrounded by the end 270 of the sleeve 218.

In one or more cases, the end 268 of the sleeve 218 includes the knob 220 attached therewith having a threaded inner surface 258. The threaded inner surface 258 of the knob 220 may be configured to rotatably engage threaded portion 234 of sleeve 216. By threading the threaded inner surface 258 with the threaded portion 234, the knob 220 and sleeve 218 may be rotatably coupled with the sleeve 216.

In one or more cases, the surgical instrument 210 may include a key 203 and cutout 205 to prevent the drive shaft 202 and the sleeve 216 from axially rotating about one another. In one or more cases, the sleeve 216 may include a cutout 205 that extends across a portion of the threaded portion 234. In one or more other cases, the cutout 205 may extend across the threaded portion 234 and into an unthreaded portion 216a of the sleeve 216. The cutout 205 may be a receptacle configured to receive the key 203 disposed on an outer surface of the driver shaft 202. The key 203 may be an elongated protrusion that extends in the direction Li and protrudes from the outer surface of the driver shaft 202. The key 203 may be configured to interlock with the cutout 205. For the cases in which the key 203 and the cutout 205 are interlocked, the driver shaft 202 and the sleeve 216 may translate through the sleeve 218, but are prevented from axially rotating about one another. That is, driver shaft 202 is prevented from axially rotating in a direction different than the axial rotation of the sleeve 216, and vice versa. In one or more other cases, the driver shaft 202 may include the cutout 205, and the sleeve 216 may include the key 203. In one or more cases, the knob 220 may include a cavity 299 that houses a spring 297 therein. On the inner surface of the cavity 299, one or more pins, such as pins 213a, 213b, and 213c may protrude from the inner surface of the cavity 299 towards the center of the cavity 299.

Figure 20B:
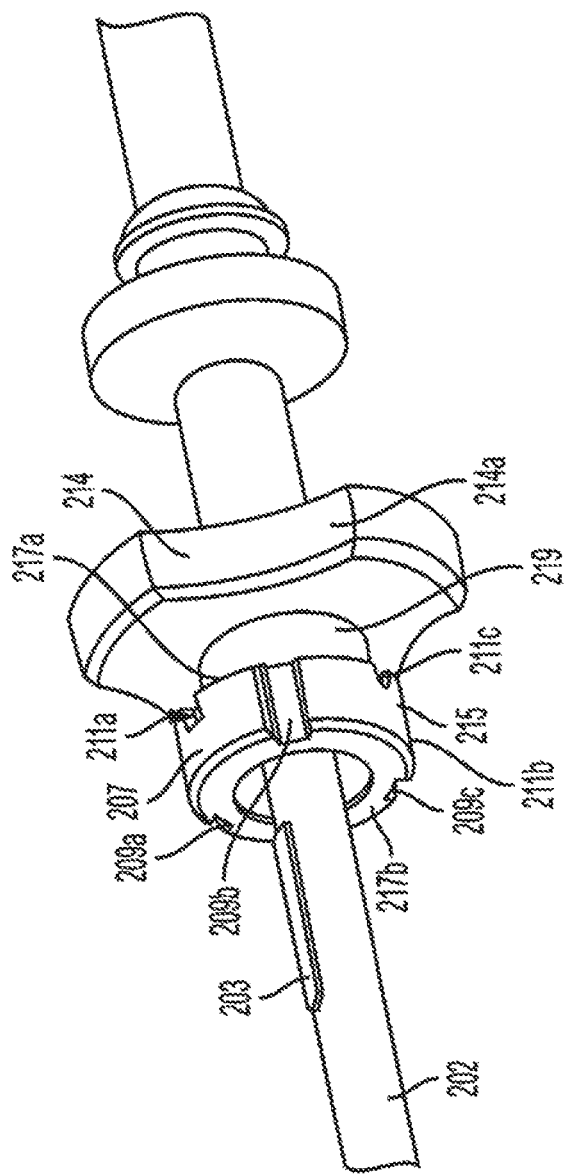
FIGS. 20B and 20C are perspective views of the components shown in FIG. 16.
Figure 20C:
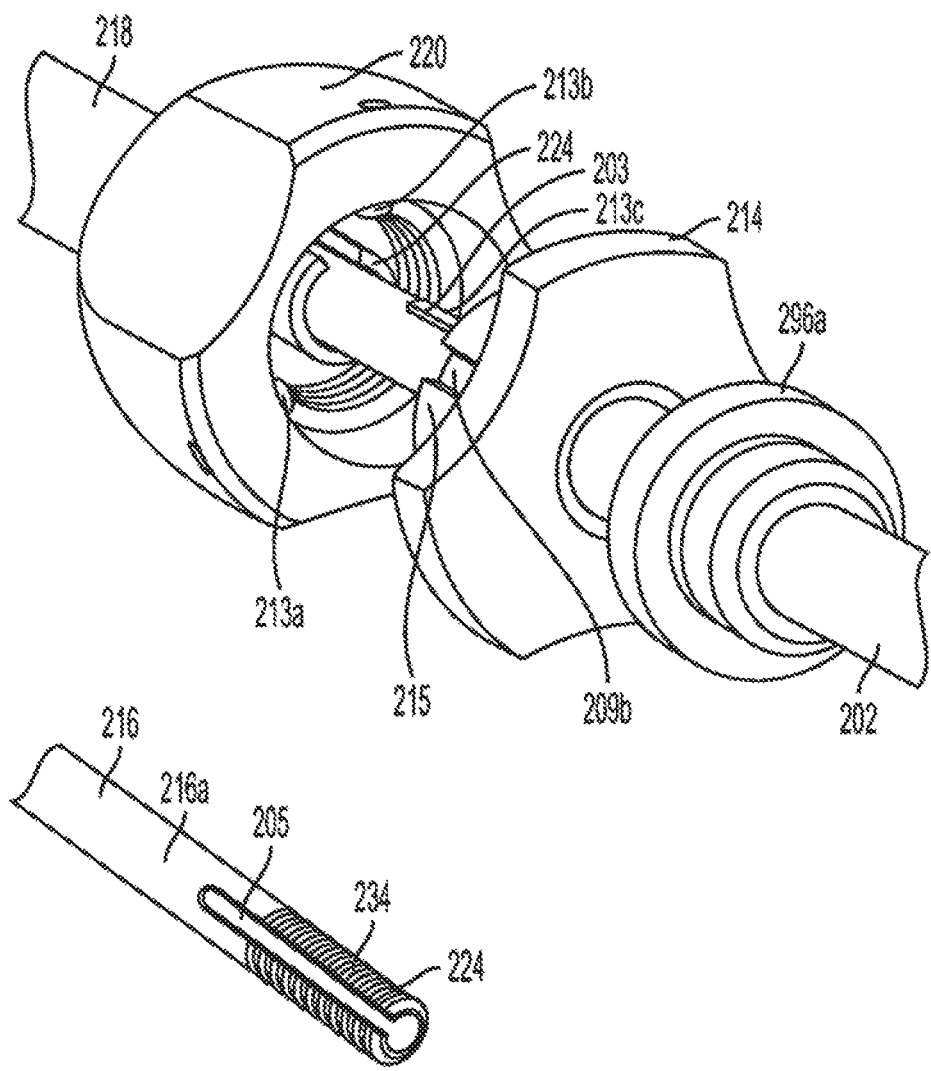

In one or more cases, the knob 214 may include an interlocking portion 215 that includes one or more tracks, such as tracks 209a, 209b, and 209c, and one or more interlocking notches, such as interlocking notches 211a, 211b, and 211c. The interlocking portion 215 may be a cylindrically rigid ring disposed on a proximal end of the knob 214. In one or more cases, each track may be recessed within the interlocking portion 215 of the knob 214. The tracks 209a, 209b, and 209c may be circumferentially disposed around the interlocking portion 215. The tracks 209a, 209b, and 209c may each extend transversely across the width of the interlocking portion 215. In one or more cases, the tracks 209a, 209b, and 209c may each be sized to accommodate a width of a pin, such as pins 213a, 213b, and 213c, therein. In one or more cases, the interlocking notches 211a, 211b, and 211c may be circumferentially disposed around the interlocking portion 215. An interlocking notch, such as interlocking notch 211a, may be positioned between two tracks, such as tracks 209a and 209b, as shown in FIG. 20B. Each interlocking notch may be notched inwards from an inner surface 217a of the interlocking portion 215. The interlocking notches 211a, 211b, and 211c may each be sized to accommodate at least a portion of a pin, such as pins 213a, 213b, and 213c, therein.

Figure 20D:
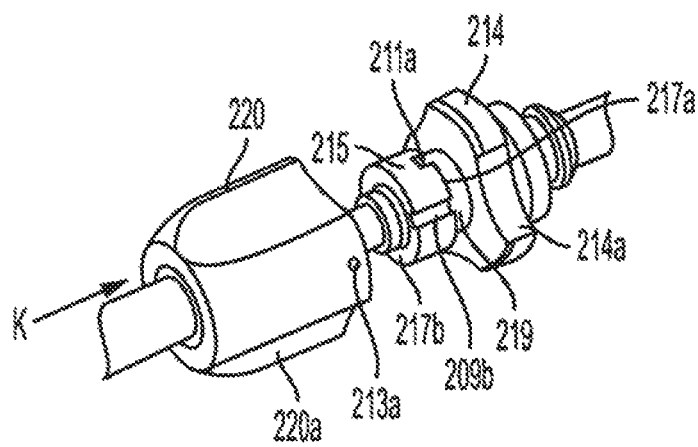
FIGS. 20D-20G are perspective views of the components shown in FIG. 16.

To assembly the sleeves 218 and/or 216 to the driver shaft 202, the knob 220 is rotated such that a pin of the knob 220 aligns with a track of the interlocking portion 215. For example, the knob 220 and/or the knob 214 may be rotated such that the pins 213a, 213b, and 213c align with the tracks 209a, 209b, and 209c and the key 203 is aligned with the cutout 205. Having aligned the one or more pins to the one or more tracks and/or the key 203 to the cutout 205, the knob 220 is moved in a direction K as shown in FIG. 20D, The one or more pins may move through their respective tracks and may be positioned over a rotation portion 219 of the knob 214. The key 203 may be inserted into the cutout 205.

Figure 20E:
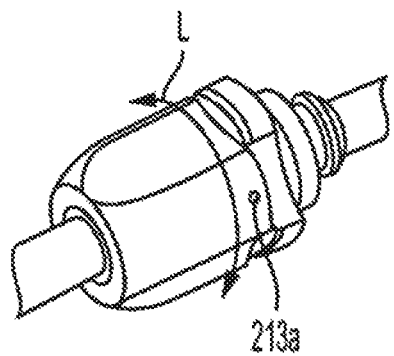
Figure 20F:
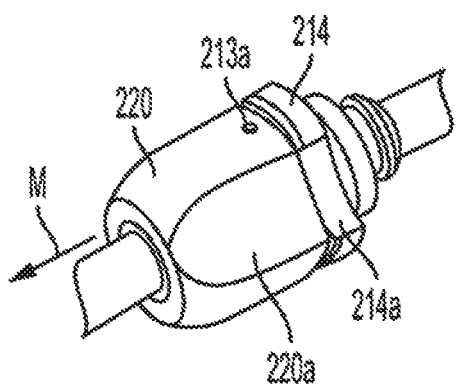
Figure 20G:
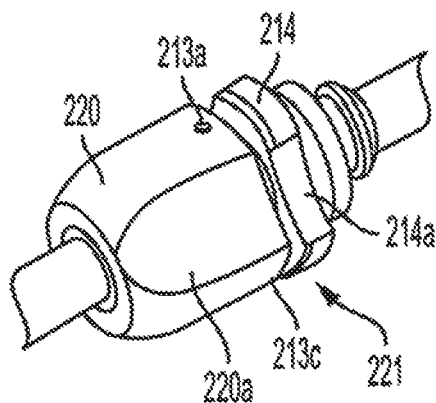

By moving the knob 220 in the direction K, an outer surface 217b of the interlocking portion 215 contacts an outer surface of the spring 297 and compresses the spring 297 in a direction 297b, as shown in FIG. 20A. Having positioned the one or more pins over the rotation portion 219, the knob 220 and/or the knob 214 are rotated in a direction L, as shown in FIG. 20E, to align the one or more pins with the one or more interlocking notches. For example, the pin 213a may be aligned with the interlocking portion 211a, the pin 213b may be aligned with the interlocking portion 211b, and the pin 213c may be aligned with the interlocking portion 211c. Having aligned the one or more pins to the one or more interlocking notches, the knob 220 may move in a direction M, as shown in FIG. 20F. At least a portion of the one or more pins may enter into and interlock with the one or more interlocking portions, respectively. For example, at least a portion of the pin 213a may be positioned within the interlocking portion 211a.

In one or more cases, the spring 297 may decompress and apply a force in a direction 297a, as shown in FIG. 20A, thereby biasing the one or more pins into the respective one or more interlocking portions. In the interlocked positioned, a space 221 may be formed indicating the one or more pins are inserted into the respective one or more interlocking portions. In one or more cases, the knob 220 may include one or more ergonomic recesses, such as recess 220a, circumferentially disposed around the knob 220. The one or more recesses 220a may be used to facilitate the rotation of the knob 220 about the driver shaft 202. In one or more cases, the knob 214 may include one or more ergonomic recesses, such as recess 214a, circumferentially disposed around the knob 214. The one or more recesses 214a may be used to facilitate the rotation of the knob 214. In one or more cases, the one or more recesses 220a of the knob 220 and the one or more recesses 214a of the knob 214 may provide a visual feedback indicating that the one or more pins are aligned with the one or more interlocking notches. For example, when the one or more recesses 220a and the one or more recesses 214a are aligned with one another and form one or more continuous recesses extending from knob 220 to knob 214, the one or more pins are aligned with the one or more interlocking notches.

The sleeve 218 is configured to lock the collet 236 with the head 238, as discussed herein, for releasable fixation with the bone fastener 222. The sleeve 218 extends along a portion of the sleeve 216 and is configured for axial translation relative to the sleeve 216. As the knob 220 rotates in a direction I as shown in FIG. 21A, the sleeve 216 axially translates, in the direction B as shown in FIGS. 21A and 21B. By axially translating the sleeve 216 in the direction B, the fingers 250a, 250b, 250c, and 250d move out of the sleeve 218. The fingers 250a, 250b, 250c, and 250d may translate over the head 238 of the fastener 222. In one or more cases, the key portions 242a and 242b of the collet 236 may be aligned with the one or more screw flats 240a of the fastener 222. As the knob 220 rotates in a direction F as shown in FIG. 21B, the fingers 250a, 250b, 250c, and 250d move into the sleeve 218 and are driven further inwardly by the force of the sleeve 218 engaging the collet 236. By engaging the sleeve 218 with the collet 236, the fingers 250a, 250b, 250c, and 250d are moved from the open position to the closed position around head 238. The knob 220 may be rotated in the direction F such that the surface 295a of the collet 236 and the surface 295b of the sleeve 218 press against one another and the sleeves 216 and/or 218 are axially rigid relative to the driver shaft 202. The rotation force tensions the fastener 222 to the end 208 of the driver shaft 202. Having engaged the fingers 250a, 250b, 250c, and 250d to the head 238 of the fastener 222, the collet 236 may be locked with the head 238.

In assembly, operation and use, a surgical implant system 200, similar to the systems and methods described herein, is employed with a surgical procedure for treatment of a spinal disorder affecting a section of a spine of a patient, as discussed herein. For example, system 200 can be used with a surgical procedure for treatment of a condition or injury of an affected section of the spine including vertebrae. In some embodiments, one or all of the components of system 200 can be delivered as a pre-assembled device or can be assembled in situ. System 200 may be completely or partially revised, removed or replaced.

For example, system 200 can be employed with a surgical treatment of an applicable condition or injury of an affected section of a spinal column and adjacent areas within a body, such as, for example, vertebrae (not shown). In some embodiments, system 200 may be employed with one or a plurality of vertebra. To treat a selected section of the vertebrae, a medical practitioner obtains access to a surgical site including the vertebrae in any appropriate manner, such as through incision and retraction of tissues. In some embodiments, system 200 can be used in any existing surgical method or technique including open surgery, mini-open surgery, minimally invasive surgery including percutaneous surgical implantation, whereby the vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of implantable components of system 200. A preparation instrument (not shown) can be employed to prepare tissue surfaces of vertebrae, as well as for aspiration and irrigation of a surgical region.

Surgical instrument 210 is disposable in a first position, as shown in FIG. 21A such that the collet 236 is in a biased closed position extending a distance from the end 270 of the sleeve 218. The mating surface 208a of the driver shaft 202 may be engaged with the mating surface 254 of the fastener 222. Rotation of the knob 220, in the direction I as shown in FIGS. 21A and 21B, causes the sleeve 216 to translate along axis Li in the direction B, as shown in FIGS. 18B and 21B. By translating the sleeve 216 in the direction B, the collet 236 may capture the head 238.

When the sleeve 216 translates out of the sleeve 218, the fingers 250a, 250b, 250c, and 250d of the collet 236 expand, in the direction C, as shown in FIG. 21B, into the biased closed position. As the fingers 250a, 250b, 250c, and 250d translate over the outer circumferential surface 278 of the fastener 222 into the open position, the fingers 250a, 250b, 250c, and 250d may expand farther in the direction C. As the fingers 250a, 250b, 250c, and 250d translate over the surface 278, the fingers 250a, 250b, 250c, and 250d are urged, due to the resilient bias of the fingers 250a, 250b, 250c, and 250d, back into the closed position in the direction D, as shown in FIG. 21B. The fingers 250a, 250b, 250c, and 250d may snap fit around the head 238, thereby capturing the head 238 within the fingers 250a, 250b, 250c, and 250d. Further rotation of the knob 220, in the direction I as shown in FIG. 21B, causes the sleeve 218 to translate in the direction E as shown in FIG. 21C, such that the end 270 of the sleeve 218 translates over the collet 236 and compresses the fingers 250a, 250b, 250c, and 250d of the collet 236. By compressing the fingers 250a, 250b, 250c, and 250d, the fingers 250a, 250b, 250c, and 250d may be tightened about the surface 278 of the head 238 to releasably fix the surgical instrument 210 with the fastener 222, thereby engaging the driver shaft 202 to rotate with the rotation of the knob 214 and/or knob 220.

In one or more cases, the driver shaft 202 may be rotated, via rotating the knob 214 and/or knob 220 in a direction A as shown in FIG. 21C. In one or more cases, the driver shaft 202 may be rotated, via rotating a handle attached to the end 204 of the driver shaft 202 or the driver shaft 202 itself in the direction A as shown in FIG. 21C. The handle, driver shaft 202, knob 214, and/or knob 220 may be rotated to apply a torsional force to the fastener 222 and increase the depth of the pilot hole and/or fasten the fastener 222 with tissue. As the depth of the pilot hole increases, the shaft 252 engages the outer layer of cortical bone such that further rotation of the fastener 222 about axis Li causes the shaft 252 to move through the pilot hole and the outer layer of cortical bone and into a layer of cancellous bone. In some embodiments, the fastener 222 is rotated until the shaft 252 of the fastener 222 penetrates the vertebra to fix the fastener 222 with the tissue. In one or more embodiments, the translation stop 288 and/or the depth stop of the surgical instrument 210 may prevent the fastener 222 from penetrating into the vertebra beyond a selected limit, as discussed herein. Rotation of the handle, driver shaft 202, knob 214, and/or knob 220 in the J direction causes the driver shaft 202 to unfasten the fastener 222 from the vertebral body.

The components of system 200, including the surgical instrument 210 and the fastener 222, are employed to augment one or more surgical treatments. The surgical instrument 210 may be disposable in the first, non-locking orientation, as described herein, to release the fastener 222 from the collet 236. To disengage the surgical instrument 210 from the fastener 222, the knob 220 is rotated in the opposite direction F, as shown in FIG. 21C, to translate sleeve 218 in the direction G as shown in FIG. 21C. Translating the sleeve 218 in the direction G may release the compression force about the collet 236. Further rotation of the knob 220 in the direction F shown in FIGS. 21B and 21C causes the sleeve 216 to translate in the direction H shown in FIGS. 18B and 21B. As the sleeve 216 translates in the direction H, the fingers 250a, 250b, 250c, and 250d move away from the head 238 and disengage the fingers 250a, 250b, 250c, and 250d from the head 238. The mating surface 208a of the driver shaft 202 may be disengaged from the mating surface 254 of the fastener 222. It is noted that the rotation direction I and direction A causes one or more components to move in the directions B and/or E, and the rotation direction J and direction A causes one or more components to move in the directions G and/or H. However, it should be understood that in one or more other cases, the rotation direction I and direction A causes one or more components to move in the directions G and/or H, and the rotation direction J and direction A causes one or more components to move in the directions B and/or E.

Surgical instrument 210 may be re-assembled for use in a surgical procedure. In some embodiments, system 200 may comprise various instruments including a lock and collet configuration of the present disclosure, with, for example, inserters, extenders, reducers, spreaders, distractors, blades, retractors, clamps, forceps, elevators and drills, which may be alternately sized and dimensioned, and arranged as a kit.

Upon completion of a procedure, surgical instrument 210, surgical instruments and/or tools, assemblies and non-implanted components of system 200 are removed and the incision(s) are closed. One or more of the components of system 200 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 200. In some embodiments, system 200 may include one or a plurality of plates, connectors and/or bone fasteners for use with a single vertebral level or a plurality of vertebral levels.

As used herein, the term "about" in reference to a numerical value means plus or minus 10% of the numerical value of the number with which it is being used.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   an elongated first member extending in a longitudinal direction from having a first end to a second end;
   a tubular second member having a third end and a fourth end, a portion of the elongated first member being positioned within a first passageway of the tubular second member; and
   a tubular third member having a fifth end and a sixth end, the portion of the elongated first member and a portion of the tubular second member being positioned within a second passageway of the tubular third member;
   a plurality of teeth provided at the sixth end of the tubular third member for boring into tissue; and
   a first handle comprising a first cavity housing the fifth end of the tubular third member and an inner surface having a first threaded portion rotatably engaged to a second threaded portion of the tubular second member;
   wherein the first handle is configured to be rotated and rotation of the first handle relative to the second threaded portion of the tubular second member urges the fifth end of the tubular third member to axially translate the tubular third member relative to the tubular second member in the longitudinal direction;
   wherein the fourth end of the tubular second member comprises an expandable member and the tubular third member has a dual purpose of boring into tissue and selectively maintaining the expandable member in a closed position; and
   wherein the plurality of teeth are configured to rotate independent of an elongated sleeve of the tubular third member.

2. The surgical instrument of claim 1, wherein the expandable member is a flexible collet configured to snap around an end of a fastener.

3. The surgical instrument of claim 1, wherein the expandable member comprises at least one key portion configured to interlock with at least one key portion disposed on an end of a fastener.

4. The surgical instrument of claim 1, wherein the first handle is configured to be rotated in a first direction to translate the sixth end of the tubular third member over the fourth end of the tubular second member.

5. The surgical instrument of claim 4, wherein the sixth end of the tubular third member is configured to compress the expandable member of the tubular second member.

6. The surgical instrument of claim 4, wherein the first handle is configured to be rotated in a second direction to translate the sixth end of the tubular third member away from the fourth end of the tubular second member.

7. The surgical instrument of claim 6, wherein the sixth end of the tubular third member is configured to decompress the expandable member of the tubular second member.

8. The surgical instrument of claim 1, wherein the tubular third member is configured to prevent the tubular second member from moving beyond a distance.

9. The surgical instrument of claim 8, wherein the tubular third member comprises one or more pins protruding into the second passageway of the tubular third member, and
wherein the tubular second member comprises one or more tracks positioned on the surface of the tubular second member and configured to receive a respective pin within the track.

10. The surgical instrument of claim 1, wherein the elongated first member includes a second handle disposed on a portion of the elongated first member, the second handle comprising a first interlock member that is configured to selectively engage a second interlock member of the first handle.

11. The surgical instrument of claim 10, wherein the elongated first member is configured to translate through the second handle.

12. A surgical system comprising:
a fastener comprising at least one key portion disposed on a surface of the fastener;
a surgical tool comprising:
an elongated first member extending in a longitudinal direction from a first end to a second end, the first end configured to engage an end of the fastener;
a tubular second member having a third end and a fourth end, a portion of the elongated first member being positioned within a first passageway of the tubular second member; and
a tubular third member having a fifth end and a sixth end, the portion of the elongated first member and a portion of the tubular second member being positioned within a second passageway of the tubular third member; and
a plurality of teeth provided the sixth end of the tubular third member for boring into tissue; and
a first handle comprising a first cavity housing the fifth end of the tubular third member and an inner surface having a first threaded portion rotatably engaged to a second threaded portion of the tubular second member;

wherein the first handle is configured to be rotated and rotation of the first handle relative to the second threaded portion of the tubular second member urges the fifth end of the tubular third member to axially translate the tubular third member relative to the tubular second member in the longitudinal direction;
wherein the fourth end of the tubular second member comprises an expandable member having at least one key portion configured to interlock with the at least one key portion of the fastener; and
wherein the plurality of teeth are configured to rotate independent of an elongated sleeve of the tubular third member.

13. The surgical system of claim 12, wherein the expandable member is a flexible collet configured to snap around the end of the fastener.

14. The surgical system of claim 12, wherein the first handle is configured to be rotated in a first direction to translate the sixth end of the tubular third member over the fourth end of the tubular second member.

15. The surgical instrument of claim 14, wherein the sixth end of the tubular third member is configured to compress the expandable member of the tubular second member.

16. The surgical instrument of claim 14, wherein the first handle is configured to be rotated in a second direction to translate the sixth end of the tubular third member away from the fourth end of the tubular second member.

17. The surgical instrument of claim 16, wherein the sixth end of the tubular third member is configured to decompress the expandable member of the tubular second member.

18. The surgical instrument of claim 12, wherein the tubular third member is configured to prevent the tubular second member from moving beyond a distance.

19. The surgical instrument of claim 18, wherein the tubular third member comprises one or more pins protruding into the second passageway of the tubular third member, and
wherein the tubular second member comprises one or more tracks positioned on the surface of the tubular second member and configured to receive a respective pin within the track.

* * * * *